US006528070B1

(12) United States Patent
Bratescu et al.

(10) Patent No.: US 6,528,070 B1
(45) Date of Patent: Mar. 4, 2003

(54) EMULSION COMPRISING A TERNARY SURFACTANT BLEND OF CATIONIC, ANIONIC, AND BRIDGING SURFACTANTS, OIL AND WATER, AND METHODS OF PREPARING SAME

(75) Inventors: Daniela T. Bratescu, Glenview, IL (US); Randal J. Bernhardt, Lindenhurst, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/662,709

(22) Filed: Sep. 15, 2000

(51) Int. Cl.$^7$ ................................................. A61K 7/00
(52) U.S. Cl. ...................... 424/401; 424/59; 514/937; 514/938
(58) Field of Search .................... 424/401, 59; 514/937, 514/938

(56) References Cited

U.S. PATENT DOCUMENTS

| | | | |
|---|---|---|---|
| 4,931,216 A | | 6/1990 | Igarashi et al. |
| 5,441,541 A | | 8/1995 | Mehreteab et al. |
| 5,607,980 A | * | 3/1997 | McAtee et al. ............. 514/476 |
| 5,622,925 A | | 4/1997 | de Buzzaccarini et al. |
| 5,661,189 A | | 8/1997 | Grieveson et al. |
| 5,939,059 A | | 8/1999 | Franklin et al. |
| 5,997,854 A | | 12/1999 | von Mallek |
| 6,007,802 A | | 12/1999 | Coffindaffer et al. |
| 6,024,952 A | | 2/2000 | Story et al. |

FOREIGN PATENT DOCUMENTS

| | | |
|---|---|---|
| JP | 62126113 | 6/1987 |
| JP | 6293620 | 10/1994 |
| JP | 2558704 | 9/1996 |
| WO | WO 97/03164 | 1/1997 |
| WO | WO 97/12022 | 4/1997 |
| WO | WO 99/58106 | 11/1999 |

* cited by examiner

*Primary Examiner*—Jose' G. Dees
*Assistant Examiner*—Konata M. George
(74) *Attorney, Agent, or Firm*—McDonnell Boehnen Hulbert & Berghoff

(57) ABSTRACT

The present invention relates to emulsions comprising an emulsification system comprising a mixture of at least one cationic surfactant, at least one anionic surfactant, at least one "bridging surfactant", an oil and water, along with methods for preparing such emulsions. More specifically, the invention relates to stable, synergistic emulsions of various oils, water, cationic, anionic, and bridging surfactants that are useful in preparing a variety of finished personal care, laundry, and cleaning products, including for examples creams, lotions, sunscreens, liquid dish detergents, laundry detergents, automatic dishwasher detergents, hand soaps, laundry bars, personal cleansing bars, multi-purpose cleaners, multi-functional shampoos, body washes, and textile treatment compositions. The emulsifications of the present invention also may be employed in agricultural and pesticide applications. Additionally, the surfactant blends may be utilized in antimicrobial formulations (e.g., antimicrobial hard surface cleaners, hand soaps, shampoos, and dish detergents), soft-terg delivery systems and pre-spotter compositions. The emulsification system of the instant invention, even when utilized in low levels, is capable allowing for the emulsification of very high levels of oils in water, whereby such emulsions are storage stable over extended periods of time at various temperatures. Additionally, concentrated emulsions of the invention are readily dilutable to very low concentrations of, and yet, are also extremely stable phase systems. The instant invention further provides sunscreen emulsions, solid particulate matter suspensions and methods of producing the same.

37 Claims, No Drawings

EMULSION COMPRISING A TERNARY SURFACTANT BLEND OF CATIONIC, ANIONIC, AND BRIDGING SURFACTANTS, OIL AND WATER, AND METHODS OF PREPARING SAME

FIELD OF THE INVENTION

The present invention relates to emulsions comprising an emulsification system comprising a mixture of at least one cationic surfactant, at least one anionic surfactant, at least one "bridging surfactant", an oil and water, along with methods for preparing such emulsions. More specifically, the invention relates to stable, synergistic emulsions of various oils, water, cationic, anionic, and bridging surfactants that are useful in preparing a variety of finished personal care, laundry, and cleaning products. The emulsification system of the instant invention, even when utilized in low levels, is capable allowing for the emulsification of very high levels of oils in water, whereby such emulsions are storage stable over extended periods of time at various temperatures. Additionally, concentrated emulsions of the invention are readily dilutable to very low concentrations, and yet, are also extremely stable phase systems. The instant invention further provides sunscreen emulsions, solid particulate matter suspensions and methods of producing the same. The emulsions of the instant invention are preferably oil-in-water emulsions, but may also be in the form of water-in-oil emulsions.

BACKGROUND OF THE INVENTION

Water-in-oil and oil-in-water emulsions have been employed in a wide variety of applications. Among these are polishes and waxes for hard surfaces of, for example, automobiles, shoes, and furniture. Emulsions are also used as antiperspirants, sunscreens, skin creams and lotions, and hair treatment compositions such as hair conditioners.

Incorporation of increased amounts of oil, and especially silicone oil, leads to difficulty in preparing stable formulations. It is particularly difficult to formulate stable emulsions having in excess of 50% by weight silicone oil. Thus, formulations of systems with oils such as silicones requires the use of an emulsification system capable of providing the requisite emulsion stability.

U.S. Pat. No. 5,188,823 discloses water-in-oil antiperspirant formulations comprising silicone oils, copolyols, phthalamic acids and/or ammonium phthalamates, and aluminum and zirconium antiperspirant salts. Water-in-oil formulations containing at most about 33% cyclomethiones are disclosed having viscosities ranging from about 2,700 to 14,000 cps. The pH of these water-in-oil formulations is from about 3.5 to 4.5. U.S. Pat. No. 5,015,415 teaches conditioning shampoos comprising phthalamic acids and/or ammonium phthalamates and silicone oils. Shampoo formulations are disclosed with no more than 0.50% silicone oil. These formulations are taught to be stable at pH values between 3 and 9.

Canadian Patent Application 2,056,859 discloses hair treatment compositions comprising a water-in-oil emulsion, wherein the water phase constitutes 40–95% by weight of the composition and the oil phase 5–60% by weight of the composition, wherein the oil phase comprises a silicone material having a viscosity of $10^4$ to $10^9$ mPas at 25° C.

Surfactant mixtures related or used in combination with emulsions are somewhat known. U.S. Pat. No. 5,441,541 (to Colgate-Palmolive) describes the use of anionic and cationic complexes to remove oily soils from fabrics. U.S. Pat. No. 5,607,980 (to Procter & Gamble) describes topical anionic and cationic compositions for application to skin. U.S. Pat. No. 5,622,925 (to Procter & Gamble) discloses heavy duty detergent compositions comprising cationic fabric softeners, fatty acids and anionic surfactants, with optional nonionics, enzymes and detergent builders. U.S. Pat. No. 6,007,802 (to Procter & Gamble) discloses mixed surfactant systems for hair care applications. U.S. Pat. No. 5,939,059 (to Akzo Nobel) discloses 2-in-1 anionic/cationic conditioning shampoos. U.S. Pat. No. 5,997,854 (to Henkel) discloses hair conditioning shampoos comprising a wide variety of components, including emulsification components. U.S. Pat. No. 6,024,952. U.S. Pat. No. 4,931,216 (to Kao) discloses anionic/cationic detergents.

For other mixed surfactant systems related to emulsions, see generally, WO 97/12022 (to Procter & Gamble); WO 97/033164 (to Procter & Gamble); WO 99/58106 (to Witco); JP 62126113; JP 6293620; and JP 2558704.

Generally, anionic-cationic surfactant mixtures are very well known to the art. See generally, U.S. Pat. Nos. 5,441,541, 5,472,455, 5,204,010, 4,790,856, 4,298,480, 3,730,912 (all to The Colgate-Palmolive Company), U.S. Pat. Nos. 5,622,925, 5,607,980, 5,565,145, 4,913,828, 4,659,802, 4,436,653, 4,338,204, 4,333,862, 4,132,680 (all to The Procter & Gamble Co.); also see WO 97/03164, WO 97/12022 and WO 96/37591 (all to The Procter & Gamble Co.), and WO 97/28238 and WO 97/15647 (both to Reckit & Colman, Inc.). See also, U.S. Pat. Nos. 5,610,187 and 4,247,538 (both to Witco Corp.), U.S. Pat. No. 5,344,949 (to Th. Goldschmidt AG), U.S. Pat. Nos. 5,332,854 and 5,324,862 (both to Dai-lchi Kogoyo Seiyaku Co., Ltd.), U.S. Pat. No. 4,273,760 (to National Starch and Chemical), and U.S. Pat. No. 4,264,457 (to DeSoto, Inc.). Mixed surfactant systems have also been disclosed in "*Mixed Surfactant Systems*", ACS Symposium Series 501, P. M. Holland and D. N. Rubingh (Jun. 17–19, 1991).

Additionally, there have been many studies and symposia on mixed surfactant systems. See, for example, Scamehorn, J. F., ed., "Phenomena in Mixed Surfactant Systems", ACS Symposium Series 311, Washington, D.C. (1986). The effects of alkyl groups and oxyethylene groups in nonionic surfactants on the surface tension of anionic-nonionic systems have been described. See Abe et al., J. Colloid Interface Sci., 107, p. 503 (1985); Ogino et al., J. Colloid Interface Sci., 107, p. 509 (1985); and Rosen et al., J. Colloid Interface Sci., 95, 443 (1983). Interaction between betaines and cationic surfactants has also been studied. See Zhu et al., J. Colloid Interface Sci., 108, 423 (1985).

Mixed surfactant systems have shown synergistic improvements in surfactant properties compared to the properties of their individual surfactant components. Synergism increases with the degree of charge difference. Thus, the greatest synergistic surfactant property improvements are realized when mixing anionic and cationic surfactants. See Rosen et al. in "Phenomena in Mixed Surfactant Systems" (Scamehorn, J. F., ed.), ACS Symposium Series 311, Washington, D.C. (1986), pp. 144–162; Zhao et al. in "Phenomena in Mixed Surfactant Systems" (Scamehorn, J. F., ed.) ACS Symposium Series 311, Washington, D.C. (1986) pp. 184–198.

In detergent applications, although in principle any surfactant is suitable, in practice only anionic and nonionic surfactants typically are used. Cationic surfactants, especially quaternary ammonium salts, can decrease detergency and enhance soil redeposition when used in heavy-duty liquid detergents. Consequently, there is a general notion that anionic and cationic surfactants cannot be used in the same formula without loss of efficacy. Similar worries regarding potential loss of efficacy exist when contemplating use of cationic surfactants in hair and skin conditioning applications. Thus, anionic-cationic surfactant mixtures have been used only sparingly in the production of consumer cleaning products and personal care products.

Studises on anionic-cationic systems are recent and few compared to studies on other mixed surfactant systems. However, strong synergism has been exhibited by these systems. Surface activity properties, particularly the critical micelle concentration (cmc), surface tension, and micro-emulsion behavior (Bourrel et al., Tenside Detergents, 21, 311 (1984)), were the most studied properties. For example, the surface activities of mixed aqueous solutions of sodium dihexylsulfosuccinate with dioctyl(hydroxyethyl) methylammonium chloride and sodium dihexylsulfosuccinate with octyl(hydroxyethyl)dimethylammonium chloride were much higher than those of the single surfactants. See Zao, G., Huoxue Xuebo, 43, 705 (1985) (Ch. Chem. Abstracts 103:184033n). The strong synergistic effect on surface pressure for mixed solutions of cationic and anionic surfactants has been studied quantitatively. When dilute solutions of sodium dodecylsulfate and dodecyltrimethylammonium bromide were mixed, tile surface pressure increased by more than 40 mN/m. Also, the cmc and the minimum surface tension were lower for the mixture than for either the anionic or cationic surfactants alone (Lucassen-Reynders et al., J. Colloid Interface Sci., 81, p. 150 (1981)).

However, mixed anionic-cationic mixtures also have shown antagonistic effects relative to the properties of the individual surfactant components. See Chobanu et al., Ilzv. Akad. Nauk. Mold. SSR, Ser. Biol. Khim. Nauk., 5, p. 66 (1982). Unlike other mixed surfactant systems, most anionic-cationic surfactant mixtures studied are insoluble or only slightly soluble in water. Hence, practical use of anionic-cationic surfactant mixtures has been very limited in areas where a relatively high concentration of surfactants is needed (see U.S. Pat. No. 5,472,455, to Mehreteab, issued Dec. 5, 1995). Also see generally, Khan, A.; Marques, E.; *Spec. Surfactants* 1997, 37–80, edited by Robb, I. D. Blackie.

Because the probability of synergism between surfactants increases with the strength of interaction, the greatest probability of synergism with anionic surfactants exists in anionic-cationic or anionic-zwiterionic mixtures. See generally, *Surfactant and Interfacial Phenomena;* Rosen, M.; John Wiley & Sons, Inc. 1989 p. 402. Surfactant performance is gauged by the so-called β value, which is a negative number indicating how much less a system's actual surface tension is compared to its calculated surface tension. Surfactant mixtures exhibiting larger deviations between calculated and actual surface tension perform better; thus, surfactant performance increases with progressively more negative β values. However, with respect to anionic-cationic mixtures, the variations in surfactant type and size that produce progressively more negative β values unfortunately are accompanied by decreasing solubility. Hence anionic-cationic synergism is limited by the formation of an insoluble salt, which typically occurs when the combined number of carbon atoms in the chains of both surfactants totals more than about twenty. See generally, Lomax, E; *Specialty Chemicals* 1993, v 13 n 4 p 223–227).

Overall, there is a strong need for emulsification systems which will allow for the emulsification of large amounts of oil, produce emulsions which are stable phases over prolonged periods of time, are stable at a variety of concentrations and at a variety of temperatures, and are dilutable and stable when diluted. Additionally, there is a strong need for sunscreen emulsions and particulate mater suspensions with similar attributes. Further such emulsions and/or suspensions should be readily formulatable in to a variety of end use products, easy to handle, and safe to handle.

SUMMARY OF THE INVENTION

The emulsions of the present invention are useful for preparing a variety of personal care, laundry, and cleaning products, including for example, creams, lotions, suncreens, hand soaps, laundry bars, personal cleansing bars, multi-purpose cleaners, multi-functional shampoos, body washes, liquid dish detergents, laundry detergents, automatic dishwasher detergents and textile treatment compositions. The emulsions of the present invention also may be employed in agricultural and pesticide applications. Additionally, the emulsions may be self-preserving (as explained in more detail below) and/or may be utilized in a variety of antimicrobial formulations (e.g., antimicrobial hard surface cleaners, hand soaps, shampoos, and dish detergents), softterg delivery systems and pre-spotter compositions.

Surprisingly, it has been discovered that complexes of anionic and cationic surfactants can be utilized in combination with a bridging surfactant to produce an emulsification system which allows for the emulsification of various oils and/or allows for the suspension of various particulate matter. The inventive emulsions and suspensions detailed herein are generally stable over a wide concentration range and at various temperatures over extend periods of time and are also surprisingly stable when diluted to low levels of oil and/or partilucate matter.

One aspect of the present invention relates to an emulsification system comprising at least one cationic surfactant, at least one anionic surfactant, and at least one "bridging surfactant". This system is useful in emulsifying oils and/or suspending solid particulate matter.

Typically, the ternary surfactant blend comprises (a) at least one cationic surfactant, (b) at least one anionic surfactant, and (c) at least one bridging surfactant, in a molar ratio of (a):(b):(c) generally of about 1:1:1. However, to optimize performance, stability and dilutability of the various emulsions and suspensions detailed herein, the molar ratio of the components can vary as conditions may dictate.

In one aspect, the invention provides a stable emulsion, comprising:
 (a) from about 0.3% to about 15% by weight, based on the total weight of the emulsion, of an emulsification system comprising:
  i) from about 0.1% to about 8% by weight, based on the total weight of the emulsion, of a cationic surfactant;
  ii) a from about 0.1% to about 8% by weight, based on the total weight of the emulsion, of an anionic surfactant;
  iii) from about 0.1% to about 8% by weight, based on the total weight of the emulsion, of a bridging surfactant;
 (b) from about 3% to about 70% by weight, based on the total weight of the emulsion, of an oil; and
 (c) from about 15% to about 97% by weight, based on the total weight of the emulsion, of water.

Generally, the emulsion comprises a stable phase at 25° C., 43° C. and/or 50° C. for 30 days. The emulsion may be diluted with water, whereby the total concentration of oil is from about 5% to about 15% by weight, based on the total weight of the diluted emulsion and the diluted emulsion is stable and comprises a stable phase at 50° C. for 30 days. Additionally, the emulsion is preferably an oil-in-water emulsion, but may also be a water-in-oil emulsion.

In another embodiment the invention provides for a stable emulsion comprising:
  (a) from about 0.3% to about 15% by weight, based on the total weight of the emulsion, of an emulsification system comprising:
    i) from about 0.1% to about 8% by weight, based on the total weight of the emulsion, of a cationic surfactant;
    ii) a from about 0.1% to about 8% by weight, based on the total weight of the emulsion, of an anionic surfactant;
    iii) from about 0.1% to about 8% by weight, based on the total weight of the emulsion, of a bridging surfactant;
  (b) from about 50% to about 70% by weight, based on the total weight of the emulsion, of an oil; and
  (c) from about 15% to about 49% by weight, based on the total weight of the emulsion, of water.

Generally, the emulsion comprises a stable phase at 25° C., 43° C. and/or 50° C. for 30 days. The emulsion may be diluted with water, whereby the total concentration of oil is from about 5% to about 15% by weight, based on the total weight of the diluted emulsion and the diluted emulsion is stable and comprises a stable phase at 50° C. for 30 days. Additionally, the emulsion is preferably an oil-in-water emulsion, but may also be a water-in-oil emulsion.

In another aspect, the invention provides for a method for preparing an emulsion comprising combining in any order:
  (a) from about 0.3% to about 15% by weight, based on the total weight of the emulsion, of an emulsification system comprising:
    i) from about 0.1% to about 8% by weight, based on the total weight of the emulsion, of a cationic surfactant;
    ii) a from about 0.1% to about 8% by weight, based on the total weight of the emulsion, of an anionic surfactant;
    iii) from about 0.1% to about 8% by weight, based on the total weight of the emulsion, of a bridging surfactant;
  (b) from about 3% to about 70% by weight, based on the total weight of the emulsion, of an oil; and
  (c) from about 15% to about 97% by weight, based on the total weight of the emulsion, of water.

The method may further comprising diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 50° C. for 30 days.

In yet another aspect, the instant invention provides for a method for preparing an emulsion comprising combining in any order:
  (a) from about 0.3% to about 15% by weight, based on the total weight of the emulsion, of an emulsification system comprising:
    i) from about 0.1% to about 8% by weight, based on the total weight of the emulsion, of a cationic surfactant;
    ii) a from about 0.1% to about 8% by weight, based on the total weight of the emulsion, of an anionic surfactant;
    iii) from about 0.1% to about 8% by weight, based on the total weight of the emulsion, of a bridging surfactant;
  (b) from about 50% to about 70% by weight, based on the total weight of the emulsion, of an oil; and
  (c) from about 15% to about 49% by weight, based on the total weight of the emulsion, of water.

The method may further comprising diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 50° C. for 30 days.

In another embodiment, the invention provides for a stable particulate matter suspension comprising:
  (a) from about 0.3% to about 15% by weight, based on the total weight of the particulate matter suspension, of a suspension system comprising:
    i) from about 0.1% to about 8% by weight, based on the total weight of the particulate matter suspension, of a cationic surfactant;
    ii) from about 0.1% to about 8% by weight, based on the total weight of the particulate matter suspension, of an anionic surfactant;
    iii) from about 0.1% to about 8% by weight, based on the total weight of the particulate matter suspension, of a bridging surfactant;
  (b) from about 3% to about 70% by weight, based on the total weight of the particulate matter suspension, of solid particulate matter; and
  (c) from about 15% to about 97% by weight, based on the total weight of the particulate matter suspension, of water.

Further, the invention provides for a stable sunscreen emulsion comprising:
  (a) from about 0.3% to about 15% by weight, based on the total weight of the sunscreen emulsion, of an emulsification system comprising:
    i) from about 0.1% to about 8% by weight, based on the total weight of the sunscreen emulsion, of a cationic surfactant;
    ii) a from about 0.1% to about 8% by weight, based on the total weight of the sunscreen emulsion, of an anionic surfactant;
    iii) from about 0.1% to about 8% by weight, based on the total weight of the sunscreen emulsion, of a bridging surfactant;
  (b) from about 3% to about 70% by weight, based on the total weight of the sunscreen emulsion, of an oil;
  (c) from about 15% to about 97% by weight, based on the total weight of the sunscreen emulsion, of water; and
  (d) from about 0.1% to about 10% by weight, based on the weight of the sunscreen emulsion, of a sunscreen.

Thus, the invention provides an ternary surfactant emulsion system comprising a synergistic mixture of anionic, cationic and bridging surfactants.

This invention further relates to personal care, laundry, and cleaning products, including for example, creams, lotions, suncreens, hand soaps, laundry bars, personal cleansing bars, multi-purpose cleaners, multi-functional shampoos, body washes, liquid dish detergents, laundry detergents, automatic dishwasher detergents and textile treatment compositions which contain the inventive emulsions.

The invention further relates to agricultural and pesticide formulations which contain the inventive emulsions.

The emulsions of the instant invention may be self-preserving (as explained in more detail below) and/or may be utilized in a variety of antimicrobial formulations.

Accordingly the instant invention relates to antimicrobial hard surface cleaners, hand soaps, shampoos, and dish detergents), soft-terg delivery systems and pre-spotter compositions which contain the inventive emulsions.

This invention further relates to oil and water emulsions containing organic sunscreens or containing organic and/or inorganic (physical) sunscreen components. It further relates to suncare/skincare compositions capable of providing a high degree of protection from the harmful effects of ultraviolet radiation, such as sunburn and sun-induced premature aging.

The surfactant compositions of the present invention optionally contain from about 0.001 percent to about 20 percent of optional ingredients such as those described in detail below and those generally selected from the group comprising anti-dandruff agents, fragrance oils, perfumes, coloring agents, dyes, sequestering agents, preservatives, pearlescenti suspending agents, thickener, viscosity modifiers, pH adjusting agents, gelling agents, opacifying agents, foam stabilizing auxiliary surfactants, silicone oils, non-volatile/nonionic silicone conditioning agents, vitamins, protein, sunscreen agents and mixtures thereof.

These and other aspects and advantages, as well as the scope, nature, and utilization of the claimed invention will become apparent to those skilled in the art from the following detailed description and claims.

DETAILED DESCRIPTION

Surprisingly, it has been found that the combination of a cationic surfactant, an anionic surfactant, and a bridging surfactant form a ternary blend which is particularly useful as an emulsification system for oil and/or a suspension system for solid particulate matter. In ternary surfactant blends of the invention, the use of additional hydrophilic groups (such as ethylene oxide groups or additional charge that remains un-neutralized during complexation) on the anionic or cationic surfactant is not necessary to produce an efficacious emulsifier system.

The present invention provides ternary surfactant emulsifier systems comprising cationic, anionic and bridging surfactants wherein anionic/cationic complexes are formed. While not intending to be limited by a particular theory, it is believed that the quaternary ammonium agent (a cationic surfactant) and anionic surfactants typically form ion pair complexes in aqueous solutions. Ternary surfactant emulsification systems of the invention are generally flowable at concentrations as high as about 80 percent by weight. The inventive emulsions prepared using the emulsification system are stable phase emulsions which are readily dilutable. Highly diluted emulsions may be clear to opaque/hazy in appearance.

The interfacial surface tension, detergency and emulsification behavior of an anionic-cationic complex is very different compared to either of the individual anionic and cationic surfactant components. In particular, an anionic-cationic complex exhibits significantly lower interfacial surface tension and significantly higher foaming than either an anionic or cationic surfactant alone. In similar fashion, the interfacial tension between certain oils and an aqueous solution of a ternary surfactant blend of the invention was found to be lower than the interfacial tension between the same oils and an aqueous solution of the individual anionic, cationic, or bridging surfactants, or combinations of two of these surfactants.

More specifically in one embodiment, the present invention provides for a stable emulsion comprising:
(a) from about 0.3% to about 15% by weight, based on the total weight of the emulsion, of an emulsification system comprising:
  i) from about 0.1% to about 8% by weight, based on the total weight of the emulsion, of a cationic surfactant;
  ii) a from about 0.1% to about 8% by weight, based on the total weight of the emulsion, of an anionic surfactant;
  iii) from about 0.1% to about 8% by weight, based on the total weight of the emulsion, of a bridging surfactant;
(b) from about 3% to about 70% by weight, based on the total weight of the emulsion, of an oil; and
(c) from about 15% to about 97% by weight, based on the total weight of the emulsion, of water.

Somewhat more preferably in this embodiment, the emulsion comprise from about 0.3% to about 10% by weight, based on the total weight of the emulsion, of the emulsification system; from about 3% to about 70% by weight, based on the total weight of the emulsion, of an oil; and from about 6% to about 95% by weight, based on the total weight of the emulsion, of water. Also some what more preferably, the cationic surfactant is a quaternary ammonium compound of the formula:

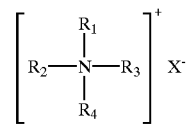

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate;
or is a compound of the general formula (I)

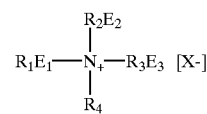

wherein X is an anion, $R_1$, $R_2$, $R_3$ can be the same or different and are independently straight or branched chain alkyl groups of from 2 to about 6 carbon atoms; R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

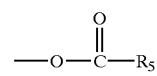

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II); or a mixture thereof. Further in accordance with this embodiment, the anionic surfactant is preferably an alkyl sulfate having an average of from about 8 to about 16 carbon atoms, an alkyl sulfonate having an average of from about 8 to about 18 carbon atoms, an alkyl ether sulfate having an average of from about 8 to about 16 carbon atoms in the alkyl portion and from about 1 to about 30 moles of ethylene oxide, an α-olefin sulfonate having an average of from about 12 to about 18 carbon atoms, an α-sulfonated $C_1$–$C_6$ alkyl ester of a fatty acid having an average of from about 11 to about 16 carbon atoms, a sulfosuccinate having an average of from about 10 to about 16 carbon atoms, a sarcosinate having an average of from about 10 to about 16 carbon atoms, a sulfoacetate having an average of from about 12 to about 20 carbon atoms, or a phthalamate, or a mixture thereof. In a highly preferred embodiment the anionic surfactant is an alkyl sulfate having an average of from about 10 to about 12 carbon atoms, an cc-sulfonated $C_{1-C6}$ alkyl ester of a fatty acid having an average of from about 11 to about 16 carbon atoms, an alkyl sulfonate having an average of about 8 carbon atoms, or a stearyl phthalamate, an alkyl ether sulfate having an average of from about 8 to about 16 carbon atoms in the alkyl portion and from about 1 to about 30 moles of ethylene oxide. or a mixture thereof. Also somewhat more preferably, the bridging surfactant selected from the group consisting of amine oxides, ethoxamides, and betaines, or a mixture thereof. The oil is preferably a silicon oil, mineral oil, a cosmetic ester or petrolatum, or a mixture thereof. Preferably, the molar ratio of cationic surfactant to anionic surfactant to bridging surfactant is about 1:1:1. Additionally, the emulsion comprises a stable phase at 25° C. for 30 days, and/or a stable phase at 43° C. for 30 days and/or a stable phase at 50° C. for 30 days. Further, the emulsion may be preferably in the form of an oil-in-water emulsion or may be in the form of a water-in-oil emulsion. The viscosity of the emulsions and/or diluted emulsions can very from thin, i.e., 100 cps, to thick cream like consistency, i.e., 80,000 cps.

A critical and surprising discovery is that the invention further provides for a diluted emulsion comprising an emulsion from the above or below embodiments, wherein the emulsion has been diluted with water, whereby the total concentration of oil is from about 5% to about 15% by weight, based on the total weight of the diluted emulsion and the diluted emulsion is stable and comprises a stable phase at 50° C. for 30 days. Typically, as known to those skilled in the are, emulsions typically break down upon dilution into multiple phases, i.e., they are not storage stable. Generally, the inventive emulsions can be diluted with water to give stable phase diluted emulsions which are stable at a variety of temperatures over extended periods of time. Generally, an emulsion is defined as a stable suspension of one liquid in a second immisible liquid. Alternatively, an emulsion can be viewed as a suspension of small globules of one liquid in a second, wherein the small globules are not totally miscible in the second liquid.

In another aspect, the invention provides a stable emulsion comprising:

(a) from about 0.3% to about 15% by weight, based on the total weight of the emulsion, of an emulsification system comprising:

i) from about 0.1% to about 8% by weight, based on the total weight of the mulsion, of a cationic surfactant of the formula:

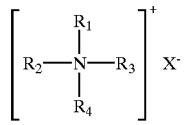

where
$R_1$, $R_2$, and $R_3$ are independently ethyl, methyl or benzyl;
$R_4$ is an alkyl group having an average of from about 8 to about 18 carbon atoms; and
X is halogen, sulfate, methosulfate, ethosulfate, tosylate, acetate, phosphate, nitrate, sulfonate, or carboxylate;
or a cationic surfactant of the formula:

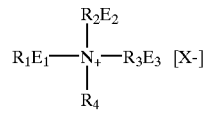

wherein X is an anion, $R_1$, $R_2$, $R_3$ can be the same or different and are independently straight or branched chain alkyl groups of from 2 to about 6 carbon atoms; R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

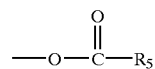

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II); or a mixture thereof;

ii) a from about 0.1% to about 8% by weight, based on the total weight of the emulsion, of an anionic surfactant which is
a) an alkyl sulfate having an average of from about 8 to about 16 carbon atoms;
b) an alkyl sulfonate having an average of from about 8 to about 18 carbon atoms;
c) an alkyl ether sulfate having an average of from about 8 to about 16 carbon atoms in the alkyl portion and from about 1 to about 30 moles of ethylene oxide;
d) an α-olefin sulfonate having an average of from about 12 to about 18 carbon atoms;
e) an α-sulfonated $C_1$–$C_6$ alkyl ester of a fatty acid having an average of from about 11 to about 16 carbon atoms;
f) a sulfosuccinate having an average of from about 10 to about 16 carbon atoms;
g) a sarcosinate having an average of from about 10 to about 16 carbon atoms;
h) a sulfoacetate having an average of from about 12 to about 20 carbon atoms;
i) a phthalamate; or mixtures thereof; and iii) from about 0.1% to about 8% by weight, based on the total weight of the emulsion, of a bridging surfactant surfactant selected from the group consisting of amine oxides, ethoxamides, and betaines, or a mixture thereof; and (b) from about 3% to about 70% by weight, based on the total weight of the emulsion, of an oil which is a silicon oil, mineral oil, a cosmetic ester or petrolatum, or a mixture thereof; and (c) from about 15% to about 97% by weight, based on the total weight of the emulsion, of water.

Preferably in accordance with this embodiment, the emulsion comprises from about 0.3% to about 10% by weight, based on the total weight of the emulsion, of the emulsification system; from about 3% to about 70% by weight, based on the total weight of the emulsion, of an oil; and from about 6% to about 95% by weight, based on the total weight of the emulsion, of water. The molar ratio of cationic surfactant to anionic surfactant to bridging surfactant is preferably about 1:1:1. Additionally, the emulsion comprises a stable phase at 25° C. for 30 days and/or a stable phase at 43° C. for 30 days and/or a stable phase at 50° C. for 30 days. The emulsion may be preferably in the form of an oil-in-water emulsion or in the form of a water-in-oil emulsion. The viscosity of the emulsions and/or diluted emulsions can very from thin, i.e., 100 cps, to thick cream like consistency, i.e., 80,000 cps.

As with the previous embodiment, a critical and surprising discovery is that the invention further provides for a diluted emulsion, in accordance with this embodiment, comprising an emulsion from the above or below embodiments, wherein the emulsion has been diluted with water, whereby the total concentration of oil is from about 5% to about 15% by weight, based on the total weight of the diluted emulsion and the diluted emulsion is stable and comprises a stable phase at 50° C. for 30 days. Generally, this inventive emulsion can also be diluted with water to give stable phase diluted emulsions which are stable at a variety of temperatures over extended periods of time.

In yet another aspect, the invention provides for a stable emulsion comprising:

(a) from about 0.3% to about 15% by weight, based on the total weight of the emulsion, of an emulsification system comprising:
i) from about 0.1% to about 8% by weight, based on the total weight of the emulsion, of a cationic surfactant;
ii) a from about 0.1% to about 8% by weight, based on the total weight of the emulsion, of an anionic surfactant;
iii) from about 0.1% to about 8% by weight, based on the total weight of the emulsion, of a bridging surfactant;

(b) from about 50% to about 70% by weight, based on the total weight of the emulsion, of an oil; and (c) from about 15% to about 49% by weight, based on the total weight of the emulsion, of water.

Suitable and/or preferable anionic, cationic, bridging surfactants, and oil are those detailed above and further below. As with the previous embodiments, a critical and surprising discovery is that the invention further provides for a diluted emulsion, in accordance with this embodiment, comprising an emulsion from the above or below embodiments, wherein the emulsion has been diluted with water, whereby the total concentration of oil is from about 5% to about 15% by. weight, based on the total weight of the diluted emulsion and the diluted emulsion is stable and comprises a stable phase at 500C for 30 days.

Generally, this inventive emulsion can also be diluted with water to give stable phase diluted emulsions which are stable at a variety of temperatures over extended periods of time. The viscosity of the emulsions and/or diluted emulsions can very from thin, i.e., 100 cps, to thick cream like consistency, i.e., 80,000 cps.

The invention provides for a method for preparing an emulsion comprising combining in any order:

(a) from about 0.3% to about 15% by weight, based on the total weight of the emulsion, of an emulsification system comprising:
i) from about 0.1% to about 8% by weight, based on the total weight of the emulsion, of a cationic surfactant;
ii) a from about 0.1% to about 8% by weight, based on the total weight of the emulsion, of an anionic surfactant;
iii) from about 0.1% to about 8% by weight, based on the total weight of the emulsion, of a bridging surfactant;

(b) from about 3% to about 70% by weight, based on the total weight of the emulsion, of an oil; and (c) from about 15% to about 97% by weight, based on the total weight of the emulsion, of water.

So The method can be practiced at a variety of temperatures, including room temperature (25° C.), i.e., cold emulsification. The method further comprises optionally diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 500C for 30 days. Suitable and/or preferable anionic, cationic, bridging surfactants, and oil are those detailed above and further below.

In another embodiment, a method for preparing an emulsion comprising combining in any order:

(a) from about 0.3% to about 15% by weight, based on the total weight of the emulsion, of an emulsification system comprising:
i) from about 0.1% to about 8% by weight, based on the total weight of the emulsion, of a cationic surfactant;
ii) a from about 0.1% to about 8% by weight, based on the total weight of the emulsion, of an anionic surfactant;
iii) from about 0.1% to about 8% by weight, based on the total weight of the emulsion, of a bridging surfactant;

(b) from about 50% to about 70% by weight, based on the total weight of the emulsion, of an oil; and (c) from about 15% to about 49% by weight, based on the total weight of the emulsion, of water.

The method can be practiced at a variety of temperatures, including room temperature (25° C.), i.e., cold emulsification. The method in accordance with this embodiment further comprises optionally diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 50° C. for 30 days. Suitable and/or preferable anionic, cationic, bridging surfactants, and oil are those detailed above and further below.

Although the ingredients can be combined in any order as described in the above methods, the invention further provides for a method whereby the cationic, anionic and bridging surfactant are premixed to form the emulsification system, which can then be combined with the water and oil.

In another aspect of the invention, a stable particulate matter suspension is provided comprising:
 (a) from about 0.3% to about 15% by weight, based on the total weight of the particulate matter suspension, of a suspension system comprising:
  i) from about 0.1% to about 8% by weight, based on the total weight of the particulate matter suspension, of a cationic surfactant;
  ii) from about 0.1% to about 8% by weight, based on the total weight of the particulate matter suspension, of an anionic surfactant;
  iii) from about 0.1% to about 8% by weight, based on the total weight of the particulate matter suspension, of a bridging surfactant;
 (b) from about 3% to about 70% by weight, based on the total weight of the particulate matter suspension, of solid particulate matter; and
 (c) from about 15% to about 97% by weight, based on the total weight of the particulate matter suspension, of water.

Suitable and/or preferable anionic, cationic, bridging surfactants, and oil are those detailed above and further below. The solid particulate matter may be a suitable material as described more fully below; preferably the solid particulate matter is an inorganic sunscreen, a powder, a pigment, an abrasive, a coal tar, an antidandruff agent or a mixture thereof. Additionally, the stable particulate matter suspension may be prepared by combining the ingredients in any order, with suitable agitation, and generally at about 25° C. Generally, a suspension is defined as a mixture of fine particles of any solid within a liquid, where by the particles are in a dispersed phase and the suspending medium is the continuous phase. The viscosity of the suspension can very from thin, i.e., 100 cps, to thick cream like consistency, i.e., 80,000 cps.

The instant invention further provides a stable sunscreen emulsion comprising:
 (a) from about 0.3% to about 15% by weight, based on the total weight of the sunscreen emulsion, of an emulsification system comprising:
  i) from about 0.1% to about 8% by weight, based on the total weight of the sunscreen emulsion, of a cationic surfactant;
  ii) a from about 0.1% to about 8% by weight, based on the total weight of the sunscreen emulsion, of an anionic surfactant;
  iii) from about 0.1% to about 8% by weight, based on the total weight of the sunscreen emulsion, of a bridging surfactant;
 (b) from about 3% to about 70% by weight, based on the total weight of the sunscreen emulsion, of an oil;
 (c) from about 15% to about 97% by weight, based on the total weight of the sunscreen emulsion, of water; and
 (d) from about 0.1% to about 10% by weight, based on the weight of the sunscreen emulsion, of a sunscreen.

Suitable and/or preferable anionic, cationic, bridging surfactants, and oil are those detailed above and further below. The sunscreen may be a suitable material as described more fully below; preferably the sunscreen is hexyl-p-methoxy-cinnamate, benzophenone-3, 2-phenylbenzimidazole-5-sulfonic acid, octyldimethyl p-amino benzoic acid, micronized titanium dioxide, or zinc oxide, or a mixture thereof. Ideally, the sunscreen absorbs UVA and UVB radiation or UVA or UVB radiation. When the the sunscreen is an inorganic sunscreen, it should ideally be capable of scattering, reflecting and absorbing UV radiation. Additionally, the sunscreen emulsion may be prepared by combining the ingredients in any order, in accordance with the other emulsion method embodiments. The sunscreen emulsion can be prepared at a variety of temperatures, including room temperature (25° C.), i.e., cold emulsification. The viscosity of the sunscreen emulsions can very from thin, i.e., 100 cps, to thick cream like consistency, i.e., 80,000 cps.

The emulsions of the invention are potentially useful, in addition to those uses described above and below, in a variety of technical applications, such as fast-break emulsifiers in personal care products; destructible latex polymerization surfactants in manufacture and compounding of various coating or adhesive systems; domestic fabric softening agents; foodstuff emulsifiers; caustic-stabile surfactants; bleach-stabile surfactants; various domestic detergents and hard surface cleaners, emulsifiers for portland cement and concrete; floatation/benefication agents for mining/processing various mineral ores; additives for electroplating and/or surface finishing for metal goods; additives for plaster, gypsum and miscellaneous building materials; enhanced oil recovery additives; wetting and lubricating agents for industrial textile processing; compatibilizers/surfactants for polyurethane/isocyanurate foam systems, wood pulping additives; emulsifiers for various industrial surfactant systems, such as fatty alcohol/water emulsions; pour-point depressants for transporting petroleum crude oils, suspension agents for various particulate materials, such as anti-dandruff materials, i.e., sulfur, zinc pyrithone, etc. and other particulate materials, such as pulverized coal, and other similar uses.

The essential, as well as the optional, components of the present invention are further described in detail below.

Cationic Surfactants

Generally, the cationic surfactant is a surfactant selected from the group comprising fatty amine salts, fatty diamine salts, polyamine salts, quaternary ammonium salts, polyoxyethyleneated fatty amine salts, quaternized polyoxyethyleneated fatty amines, and mixtures thereof. A variety of cationic surfactants useful in the present invention are well known in the art. Cationic surfactants useful herein include those disclosed in the following documents, all of which are incorporated by reference herein: M. C. Publishing Co., *McCutcheon's Detergents & Emulsifiers*, (North American Ed., 1993); Schwartz et al., *Surface Active Agents, Their Chemistry and Technology,* New York; Interscience Publisher, 1949; U.S.

U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983. Suitable anions include but are not limited to halogen, sulfate, methosulfate, ethosulfate, tosylate, acetate, phosphate, nitrate, sulfonate, and carboxylate.

Cationic surfactants in the form of quaternary ammonium salts include mono-long chain alkyl-tri-short chain alkyl ammonium halides, wherein the long chain alkyl group has from about 8 to about 22 carbon atoms and is derived from long-chain fatty acids, and wherein the short chain alkyl groups can be the same or different but preferably are independently methyl or ethyl. Examples of quaternary ammonium salts useful herein include but are not limited to cetyl trimethyl ammonium chloride and lauryl trimethyl ammonium chloride. A particularly preferred quaternary ammonium salt is cetyl trimethyl ammonium chloride.

Salts of primary, secondary and tertiary fatty amines are also suitable cationic surfactant materials. The alkyl groups of such amine salts preferably have from about 12 to about 22 carbon atoms, and may be substituted or unsubstituted. Secondary and tertiary amine salts are preferred, tertiary amine salts are particularly preferred. Suitable amine salts include the halogen (i.e fluoride, chloride, bromide), acetate, phosphate, nitrate, citrate, lactate and alkyl sulfate salts. Amine salts derived from amine, such as for example, stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine, are useful herein. Such salts also include stearylamine hydrogen chloride, soyamine chloride, stearylamine formate, N-tallowpropane diamine dichloride and stearamidopropyl dimethylamine citrate. Additionally cationic surfactants included among those useful in the present invention are disclosed in U.S. Pat. No. 4,275,055, Nachtigal, et al., issued Jun. 23, 1981, incorporated herein by reference.

In addition to the above, cationic surfactants particularly useful herein are those of the general formula:

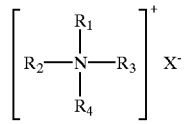

where $R_1$, $R_2$, and $R_3$ are independently ethyl, methyl or benzyl; $R_4$ is an alkyl group having an average of from about 8 to about 16 carbon atoms; and X is an a suitable ion including but not limited to halogen, sulfate, methosulfate, ethosulfate, tosylate, acetate, phosphate, nitrate, sulfonate, or carboxylate.

Other quaternary ammonium compounds and amine salt compounds include those of the above general formula in the form of ring structures formed by covalently linking two of the radicals. Examples include imidazolines, imidazoliniums, and pyridiniums, etc., wherein said compound has at least one nonionic hydrophile-containing radical as set forth above. Specific examples include 2-heptadecyl-4,5-dihydro-1H-imidazol-1-ethanol, 4,5-dihydro-1-(2-hydroxyethyl)-2-isoheptadecyl-1phenylmethylimidazolium chloride, and 1-[2-oxo-2-[[2-[(1-oxoctadecyl)oxy]ethyl]amino]ethyl] pyridinium chloride. Additionally, useful polymerizable surface active agents include those of the above general formula in the form of ring structures formed by covalently linking two of the $R_1$-$R_4$ groups.

The quaternary ammonium salts of the present invention may be prepared by a variety of methods known to the art, including for example, halide exchange, wherein a halide based quaternary ammonium compound is ion exchanged with X, where X is defined above.

The most preferred cationic surfactants for use in the present invention include octyltrimethyl ammonium chloride, decyltrimethyl ammonium chloride, dodecyltrimethyl ammonium bromide, dodecyltrimethyl ammonium chloride, AMMONYX® CETAC-30, BTC®-65NF, BTC®-835 and BTC®-885, all commercially available from Stepan Company.

Other cationic surfactants includes those compounds commonly referred to as "ester quats", and as disclosed in U.S. Pat. No. 5,939,059 (incorporated herein in its entirety). Typically, such materials are of the general formula

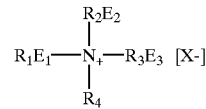

wherein X is an anion, $R_1$, $R_2$, $R_3$ can be the same or different and are independently straight or branched chain alkyl groups of from 2 to about 6 carbon atoms; R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

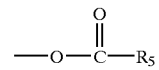

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II).

Additionally, a quaternary ammonium compound of the formula:

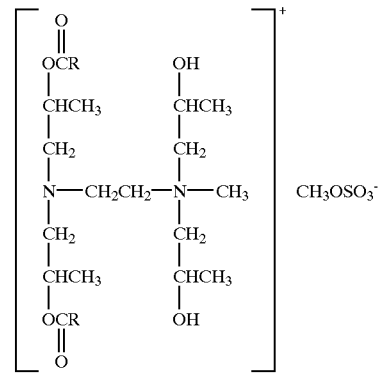

where R is substantially linear nor-oleyl, may be used in the various inventive blends. This material, also called STEPANQUAT™ ML, is commercially available from Stepan Company, Northfield, Ill. Additionally, the cationic surfactant may be a di-quaternary or poly quaternary compound. The cationic surfactant may also be a DMAPA amidoamine based quaternary ammonium material.

Further, the cationic can also be an antimicrobial compound of the formula:

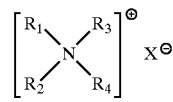

wherein $R_1$ and $R_2$ are straight or branched chain lower alkyl groups having from one to seven carbon atoms; $R_3$ is a straight or branched chain higher alkyl group having from about eight to twenty carbon atoms, or a benzyl group optionally substituted with $C_1$–$C_6$ alkyl; $R_4$ is a straight or branched chain higher alkyl group having from about eight to twenty carbon atoms; and X is an anion forming a water soluble salt, such as, halogen, methosulfate, saccharinate, sulfate, ethosulfate, tosylate, acetate, phosphate, nitrate, sulfonate, or carboxylate. With regard to use of these types of cationic materials, the emulsions and/or suspensions of the instant invention can be considered self-preserving, whereby the growth of micro-organisms is inhibited by the presence of such materials, without the use of additional antimicrobial compounds or preservatives.

Further illustrative of suitable quaternary ammonium microbiocides are dioctyl dimethyl ammonium chloride, octyl decyl dimethyl ammonium chloride, didecyl dimethyl ammonium chloride, ($C_{12}$–$C_{18}$) n-alkyl dimethyl benzyl ammonium chloride, ($C_{12}$–$C_{18}$) n-alkyl dimethyl ethylbenzyl ammonium chloride, and ($C_{12}$–$C_{18}$) n-alkyl dimethyl benzyl ammonium saccharinate. This is not an exhaustive list and other quaternary ammonium salts having microbiocidal activity will suffice. The quaternary ammonium salt in the present invention need not be a single entity, but may be a blend of two or more quaternary ammonium salts.

The following quaternary ammonium compounds may be efficiently used in the compositions of the invention:

| | |
|---|---|
| BTC 1010 | didecyl dimethyl ammonium chloride |
| BTC 1010-80% | didecyl dimethyl ammonium chloride |
| BTC 2125m | n-alkyl dimethyl benzyl ammonium chlorides (and) n-alkyl dimethyl ethylbenzyl ammonium chlorides |
| BTC 2125m p40 | n-alkyl dimethyl benzyl ammonium chlorides (and) n-alkyl dimethyl ethylbenzyl ammonium chlorides |
| BTC 2125m-80% | n-alkyl dimethyl benzyl ammonium chlorides (and) n-alkyl dimethyl ethylbenzyl ammonium chlorides |
| BTC 2125m-90% | n-alkyl dimethyl benzyl ammonium chlorides (and) n-alkyl dimethyl ethylbenzyl ammonium chlorides |
| BTC 2565 | n-alkyl dimethyl benzyl ammonium chloride |
| BTC 2568 | n-alkyl dimethyl benzyl ammonium chloride |
| BTC 50 nf | n-alkyl dimethyl benzyl ammonium chloride |
| BTC 65 nf | n-alkyl dimethyl benzyl ammonium chloride |
| BTC 776 | n-alkyl dimethyl benzyl ammonium chloride and -dialkyl methyl benzyl ammonium chloride |
| BTC 818 | dialkyl dimethyl ammonium chloride |
| BTC 818-80% | dialkyl dimethyl ammonium chloride |
| BTC 824 | n-alkyl dimethyl benzyl ammonium chloride |
| BTC 824 p100 | n-tetradecyl dimethyl benzyl ammonium chloride monohydrate |
| BTC 8248 | n-alkyl dimethyl benzyl ammonium chloride |
| BTC 8249 | n-alkyl dimethyl benzyl ammonium chloride |
| BTC 835 | n-alkyl dimethyl benzyl ammonium chloride |
| BTC 8358 | n-alkyl dimethyl benzyl ammonium chloride |
| BTC 885 | n-alkyl dimethyl benzyl ammonium chloride and dialkyl dimethyl ammonium chloride |
| BTC 888 | n-alkyl dimethyl benzyl ammonium chloride and dialkyl dimethyl ammonium chloride |
| BTC 99 | didecyl dimethyl ammonium chloride |

Each is commercially available from Stepan Company, Northfield, Ill. 60093.

Preferred antimicrobial cationic compounds of the invention include BTC 65NF,. BTC 835, BTC 2125M, BTC 2125M P40, BTC 2125M-80%, and BTC 2125M-90%.

Anionic Surfactants

The anionic surfactants that may be utilized according to the present invention are well known to the art and are described below in a representative manner. Generally speaking, a variety of anionic surfactants useful in the present invention are well known in the art. Anionic surfactants useful herein include those disclosed in the following documents, all of which are incorporated by reference herein: M. C. Publishing Co., *McCutcheon's Detergents & Emulsifiers,* (North American Ed., 1993); Schwartz et al., *Surface Active Agents, Their Chemistry and Technology,* New York; Interscience Publisher, 1949; U.S. Pat. No. 4,285,841, Barrat et al, issued Aug. 25, 1981; and U.S. Pat. No. 3,919,678, Laughlin et al, issued Dec.30, 1975.

The anionic surfactants of the present invention generally include salts (including, for example, sodium, potassium, ammonium, and substituted ammonium salts such as mono-, di-, and triethanolamine salts) of the anionic sulfate, sulfonate, carboxylate and sarcosinate surfactants. Other suitable anionic surfactants include the isethionates such as the acyl isethionates, N-acyl taurates, fatty acid amides of methyl tauride, alkyl succinates, sulfoacetates, and sulfosuccinates, monoesters of sulfosuccinate (especially saturated and unsaturated $C_{12}$–$C_{18}$ monoesters), diesters of sulfosuccinate (especially saturated and unsaturated $C_6$–$C_{14}$ diesters), and N-acyl sarcosinates. Resin acids and hydrogenated resin acids are also suitable, such as rosin, hydrogenated rosin, and resin acids and hydrogenated resin acids present in or derived from tallow oil.

Anionic sulfate surfactants suitable for use in the compositions of the invention include the linear and branched primary and secondary alkyl sulfates, alkyl ethoxysulfates, fatty oleyl glycerol sulfates, alkyl phenol ethoxylate sulfates, alkyl phenol ethylene oxide ether sulfates, the $C_5$–$C_{17}$ acyl-N-($C_1$–$C_4$ alkyl) and -N-($C_1$–$C_2$ hydroxyalkyl) glucamine sulfates, and sulfates of alkylpolysaccharides such as the sulfates of alkylpolyglucoside.

Alkyl sulfate surfactants are preferably selected from the group consisting of the $C_8$–C22 alkyl sulfates. Most preferably, the alkyl sulfate surfactant is a $C_8$–$C_{16}$ alkyl sulfate. Alkyl ethoxysulfate surfactants are preferably selected from the group consisting of the $C_8$–$C_{22}$ alkyl sulfates that have been ethoxylated with from about 0.5 to about 30 moles of ethylene oxide per molecule. Most preferably, the alkyl ethoxysulfate surfactant is a $C_8$–$C_{16}$ alkyl sulfate which has been ethoxylated with from about 1 to about 30 moles of ethylene oxide.

A particularly preferred anionic surfactant comprises mixtures of $C_8$ alkyl sulfate (POLYSTEP® B-29, commercially available from Stepan Company, Northfield, Ill.) and alkyl ethoxysulfate surfactants. Such mixtures have been disclosed in WO 93/18124, incorporated by reference herein.

Anionic sulfonate surfactants suitable for use herein include the salts of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonate alkyl glycerol sulfonates, fatty acyl glycerol sulfonates, fatty oleyl glycerol sulfonates, and any mixtures thereof.

Anionic sulfonate surfactants are preferably selected from the group consisting of the $C_8$–$C_{22}$ alkyl sulfonates and $C_8$–$C_{22}$ α-olefin sulfonates. Most preferably, the anionic sulfonate surfactant is an $C_8$–$C_{18}$ alkyl sulfonate, such as BIOTERGE® PAS-8S (commercially available from Stepan Company, Northfield, Ill.), or a $C_{12}$–$C_{18}$ α-olefin sulfonate, such as BIOTERGE® AS-40 (commercially available from Stepan Company, Northfield, Ill.).

Suitable anionic carboxylate surfactants include the alkyl ethoxy carboxylates, the alkyl polyethoxy polycarboxylate surfactants and the soaps ("alkyl carboxyls"), especially certain secondary soaps as described herein.

Suitable alkyl ethoxy carboxylates include those with the formula $RO(CH_2CH_2O)_xCH_2COO^-M^+$ wherein R is a $C_6$ to $C_8$ alkyl group, x ranges from 0 to 10, and the ethoxylate distribution is such that, on a weight basis, the amount of material where x is 0 is less than about 20 percent and M is a cation. Suitable alkyl polyethoxy polycarboxylate surfactants include those having the formula $RO(CHR_1CHR_2O)R_3$ wherein R is a $C_6$ to $C_{16}$ alkyl group, x ranges from 1 to 25, $R_1$ and $R_2$ from the group consisting of hydrogen, methyl acid radical, succinic acid radical, hydroxysuccinic acid radical, and mixtures thereof, and $R_3$ is selected from the group consisting of hydrogen, substituted or unsubstituted hydrocarbon having between 1 and 8 carbon atoms, and mixtures thereof.

Suitable anionic soap surfactants include the secondary soap surfactants which contain a carboxyl unit connected to a secondary carbon. Preferred secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid.

Suitable anionic sulfosuccinates include those having the formula

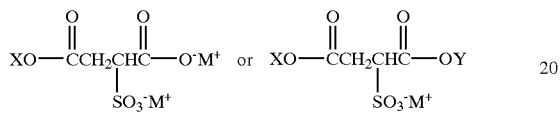

where

X and Y are the same or different and are selected from the group consisting of R and R(CH$_2$CH$_2$O)$_x$, where x has an average value from about 1 to about 30;

R is C$_8$–C$_{22}$ alkyl;

and M is an counterion.

Anionic sulfosuccinate surfactants are preferably selected from the group consisting of the C$_8$–C$_{22}$ sulfosuccinates. Most preferably, the anionic sulfosuccinate surfactants is a mono -C$_{10}$–C$_{16}$ alkyl sulfosuccinate such as disodium laureth sulfosuccinate (STEPAN-MILD® SL3, commercially available from Stepan Company, Northfield, Ill.)

Other suitable anionic surfactants are the sarcosinates of the formula RCON(R$_1$)CH$_2$COOM, wherein R is a C$_5$–C$_{22}$ linear or branched alkyl or alkenyl group, R. is a C$_1$–C$_4$ alkyl group and M is an ion. Preferred sarcosinate surfactants include but are not limited to the myristyl and oleoyl methyl sarcosinates in the form of their sodium salts. Most preferably, the sarcosinate surfactant is a C$_{10}$–C$_{16}$ sarcosinate such as MAPROSYLO® 30 (commercially available from Stepan Company, Northfield, Ill.).

Other suitable anionic surfactants are the alkyl sulfoacetates of the formula RO(CO)CH$_2$SO$_3$M, wherein R is a C$_{12}$–C$_{20}$ alkyl group and M is an ion. Preferred aalkyl sulfoacetates include but are not limited to the lauryl and myristyl sulfoacetates in the form of their sodium salts. Most preferably, the alkyl sulfoacetate is LATHANOL® LAL (commercially available from Stepan Company, Northfield, Ill.).

The anionic surfactant may comprise a) from about 3% to about 25% by weight based on the total weight of the composition of an alpha sulfonated alkyl ester of the formula

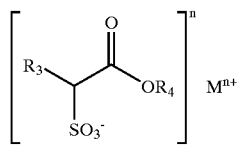

wherein $R_3$ is a C$_6$–C$_{22}$ hydrocarbyl group, an alkyl group, or combination thereof, $R_4$ is a straight or branched chain C$_1$–C$_6$ hydrocarbyl group, an alkyl group, or combination thereof, n is 1 or 2 and M is hydrogen, sodium, potassium, calcium, magnesium, ammonium, monoethanolammonium, diethanolammonium, triethanolammonium, or a mixture thereof; and b) from about 0.01% to about 15% by weight based on the total weight of the composition of a sulfonated fatty acid of the formula

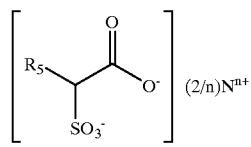

wherein $R_5$ is a C$_6$–C$_{22}$ hydrocarbyl group, an alkyl group, or combination thereof, n is 1 or 2 and wherein N is hydrogen, sodium, potassium, calcium, magnesium, ammonium, monoethanolammonium, diethanolammonium, triethanolammonium, or a mixture thereof; and wherein the weight ratio of i) to ii) is from about 10:1 to about 0.5:1. Additionally, the alkyl $R_3$ and/or $R_5$ groups can be a straight, branched, mid-chain branched or cyclic alkyl groups in form.

The alpha sulfonated alkyl esters used in the invention are typically prepared by sulfonating an alkyl ester of a fatty acid with a sulfonating agent such as SO$_3$, followed by neutralization with a base, such as sodium hydroxide, potassium hydroxide, calcium hydroxide, magnesium oxide, monoethanolamine, diethanolamine or triethanolamine, or a mixture thereof. When prepared in this manner, the alpha sulfonated alkyl esters normally contain a minor amount, typically not exceeding 33% by weight, of alpha sulfonated fatty acid, i.e., disalt, which results from hydrolysis of the ester. Generally, larger amounts of the disalt are obtained by hydrolyzing a known amount of the monosalt; hydrolysis may be accomplished in situ during the preparation of the composition. Accordingly, the alpha sulfonated alkyl ester and alpha sulfonated fatty acid may be provided to the composition (or utilized in the inventive process) as a blend of components which naturally result from the sulfonation of an alkyl ester of a fatty acid, or as individual components. Furthermore, it is known to one skilled in the art that minor impurities such as sodium sulfate, unsulfonated methyl esters (ME), and unsulfonated fatty acids (FA) may also be present in the mixtures according to the invention.

The alpha sulfonated alkyl esters, i.e., alkyl ester sulfonate surfactants, include linear esters of C$_6$–C$_{22}$ carboxylic acid (i.e., fatty acids) which are sulfonated with gaseous SO$_3$ according to the "The Journal of American Oil Chemists Society," 52 (1975), pp. 323–329. Suitable starting materials include, among others, natural fatty substances as derived from tallow, palm oil, etc. Suitable anionic α-sulfonated methyl ester surfactant also include ALPHA STEP® MC-48 or ALPHA STEP® ML-40 (both commercially available from Stepan Company, Northfield, Ill.).

The phthalate anionic surfactants useful herein have the general formula:

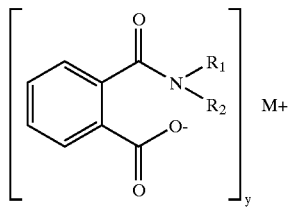

wherein $R_1$ and $R_2$ are independently selected from the group consisting essentially of H or $C_1$–$C_{40}$ linear or branched, substituted or unsubstituted alkyl, cycloalkyl, alkylene, alkaryl, aryl or $R_3$—O—$R_4$ groups, with $R_3$ and $R_4$ being independently selected from the group consisting essentially of $C_1$–$C_{22}$ linear or branched, substituted or unsubstituted alkyl, cycloalkyl, alkylene, alkaryl and aryl groups; y is an integer of a value satisfying the valency of M; and M is a cation and is preferably selected from the groups consisting of H, Na, K, $NH_4$ [including $(CH_3CH_2)_3$NH, $(CH_3CH_2)_2NH_2$, $(HOCH_2CH_2)_3NH$, $(HOCH_2CH_2)_2NH_2$ and similar ammonium derivatives], Ba, Ca, Mg, Al, Ti, Zr and mixtures thereof. These materials may be prepared as generally disclosed in WO 91/01970 (to Stepan Company), incorporated in its entirety.

Other anionic surfactant useful in the present invention N,N-disubstituted phthalamic acids and their salts as generally disclosed in U.S. Pat. Nos. 5,015,415 and 5,188,823 (both to Stepan Company), incorporated herein in their entirety. Phosphate esters are also generally useful anionic surfactants.

Bridging Surfactants

The bridging surfactants of the present invention are selected from the group consisting of semi-polar nonionic (i.e., amine oxides), ethoxamide, and amphoteric surfactants (i.e., betaines) and mixtures thereof. Especially preferred bridging surfactants include amine oxides, ethoxylated alkanolamides, and betaines.

Semi-polar nonionic surfactants include water-soluble amine oxides having an alkyl moiety containing from about 10 to about 18 carbon atoms and 2 moieties selected from the group consisting of alkyl groups and hydroxyalkyl groups containing from about 1 to about 3 carbon atoms. Semi-polar nonionic surfactants also include water-soluble sulfoxides having alkyl moieties containing from about 10 to about 18 carbon atoms and a moiety selected from the group comprising alkyl groups and hydroxyalkyl groups of from about 1 to about 3 carbon atoms.

The present invention encompasses semi-polar nonionic surfactants that are amine oxides formed as shown in Scheme I, wherein $R_1$, $R_2$, $R_3$ independently are substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain; and wherein X is an anion group selected from the group consisting of halogen, sulfonate, sulfate, sulfinate, sulfenate, phosphate, carboxylate, nitrate, and acetate. Additionally, useful semi-polar nonionic surfactants include those of the below general formula in the form of ring structures formed by covalently linking two of the $R_1$–$R_4$ groups. Examples include unsaturated imidazolines, imidazoliniums, and pyridiniums, and the like. Particularly preferred semi-polar nonionic surfactants include alkylamine and amidoamine oxides.

Scheme I:
Amine Oxide-Derived Surface Active Agents

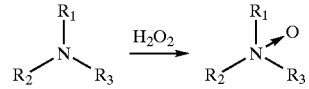

Particularly preferred amine oxides include but are not limited to AMMONYX® C8 (octylamine oxide), AMMONYX° C10 (decylamine oxide), AMMONYX® LO (laurylamine oxide), AMMONYX® MO (myristylamine oxide), AMMONXY® MCO (myristyl/cetylamine oxide), and AMMONYXO CDO (cocamidoproylamine oxide), all commercially available from Stepan Company, Northfield, Ill. Amine oxide surfactants which are generally suitable for use in the present invention are alkylamine and amidoamine oxides.

Other Examples of betaines and sultaines which are suitable for use in the present invention are alkyl betaines and sultaines sold as "Mirataine"® by Rhone Poulenc, "Lonzaine"® by Lonza, Inc., Fairlawn, N. J. Examples of betaines and sultaines are cocobetaine, cocoamidoethyl betaine, cocoamidopropyl betaine, lauryl betaine, lauramidopropyl betaine, palmamidopropyl betaine, stearamidopropyl betaine, stearyl betaine, coco-sultaine, lauryl sultaine, tallowamidopropyl hydroxysultaine and the like.

Ethoxamids (also termed ethoxylated alkanolamides or polyethylene glycol amides) suitable for use in the present invention include those having the formula

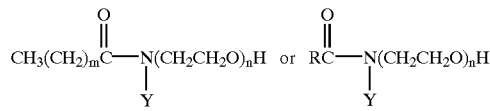

where
RCO—represents the fatty acids derived from coconut oil;
m is an integer from about 8 to about 16;
n has an average value of about 3;
Y is hydrogen or $(CH_2CH_2O)_pH$; and
p is 0, 1 or more.

Preferred ethoxamides include but are not limited to AMIDOX® C-2 (PEG-3 cocamide), AMIDOX® C-5 (PEG-6 cocamide), and AMIDOXO® L-5 (PEG-6 lauramide), all commercially available from Stepan Company, Northfield, Ill.

Suitable amphoteric surfactants are selected from the group consisting of alkyl glycinates, propionates, imidazolines, amphoacetates, amphoalkylsulfonates (sold under the tradename Miranol® by Rhone Poulenc), N-alkylaminopropionic acids, N-alkyliminodipropionic acids, imidazoline carboxylates, N-alkylbetaines, amido propyl betaines, sarcosinates, cocoamphocarboxyglycinates, amine oxides, sulfobetaines, sultaines and mixtures thereof. Additional suitable amphoteric surfactants include cocoamphoglycinate, cocoamphocarboxyglycinate, lauramphocarboxyglycinate, coco-amphopropionate, lauramphopropionate, stearamphoglycinate, cocoamphocarboxypropionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, caprylamphopropylsulfonate, cocamphopropylsulfonate, stearamphopropylsolfonate, oleoampho-propylsulfonate and the like.

Examples of betaines and sultaines which are suitable for use as bridging surfactants are alkyl betaines and sultaines sold under the tradename Mirataine® by Rhone Poulenc, and Lonzaine® by Lonza, Inc., Fairlawn, N. J. Additional examples of betaines and sultaines include cocobetaine, cocoamidoethyl betaine, cocoamidopropyl betaine, lauryl betaine, lauramidopropyl betaine, palmamidopropyl betaine, stearamidopropyl betaine, stearyl betaine, cocosultaine, lauryl sultaine, tallowamidopropyl hydroxysultaine and the like. Particularly preferred amphoteric surfactants include AMPHOSOL® CA (cocamidopropyl betaine) and AMPHOSOL® DM (lauryl betaine), both commercially available from Stepan Company, Northfield, Ill.

Other betaines useful in the present invention include compounds having the formula $R(R_1)_2N^+R_2COO^-$ wherein R is a $C_6-C_{18}$ hydrocarbyl group, preferably $C_{10}-C_{16}$ alkyl group, each $R_1$ is typically $C_1-C_3$, alkyl, preferably methyl, and $R_2$ is a $C_1-C_5$ hydrocarbyl group, preferably a $C_1-C_5$ alkylene group, more preferably a $C_1-C_2$ alkylene group. Examples of suitable betaines include coconut acylamidopropyldimethyl betaine; hexadecyl dimethyl betaine; C12–C14 acylamidopropylbetaine; $C_8-C_{14}$ acylamidohexyidiethyl betaine; 4-$[C_{14}-C_{16}$ acylmethylamidodiethylammonio]-1-carboxybutane; $C_{16}-C_{18}$ acylamidododimethylbetaine; $C_{12}-C_{16}$ acylamidopentanediethylbetaine; $C_{12}-C_{16}$ acylmethylamidodimethylbetaine. Preferred betaines are $C_{12}-C_{18}$ dimethylamoniohexanoate and the $C_{10}-C_{18}$ acylamidopropane (or ethane) dimethyl (or diethyl) betaines.

Other sultaines useful in the present invention include compounds having the formula $R(R_1)_2N^+R_2SO_3^{31}$, wherein R is a $C_6-C_{18}$ hydrocarbyl group, preferably a $C_{10}-C_{16}$ alkyl preferably a $C_{12}-C_{13}$ alkyl group; each $R_1$ is typically $C_1-C_3$ alkyl, preferably methyl and $R_2$ is a $C_1-C_6$ hydrocabyl group, preferably a $C_1-C_3$ alkylene or, preferably, hydroxyalkylene group. Examples of suitable sultaines are $C_{12}-C_{14}$ dihydroxyethylammino propane sulfonate, and $C_{16}-C_{18}$ dimethylammonio hexane sulfonate, with $C_{12}-C_{14}$ amido propyl ammonio-2-hydroxypropyl sultaine being preferred.

Oil Ingredients

The oil component may generally comprise one or more hydrophobic materials. These materials are hydrophobic oils that are insoluble in water. Representative oils suitable for use in the inventive compositions include, but are not limited to silicon oil, mineral oil, a cosmetic ester or petrolatum, or a mixture thereof. Suitable cosmetic esters include for example, STEPAN™ IPM (isopropyl myristate) STEPAN™ IPP (isopropyl palmitate), STEPAN™ OCTYL PALMITATE (octyl palmitate), STEPAN™ OCTYL ISONONANOATE (octyl isononanoate), STEPAN™ ICS (isocetyl stearate). STEPAN™ BS (butyl stearate), STEPAN™ 653 (cetyl palmitate), STEPAN™ 654 (cetyl myristate), STEPAN™ CETYL ALCOHOL (cetyl alcohol), all commercially available from Stepan Company (Northfield, Ill.).

Other non-limiting examples of useful oil include crude petroleum oil, distilled petroleum oil, heavy paraffinic oil, asphaltene oil, linseed oil, tall oil, soybean oil alkyd, linseed oil alkyd, isopropyl palmitate (IPP)₁ isopropyl myristate, caprylic/capric triglyceride, lanolin, acetylated lanolin alcohol, dimethicone, hydrogenated vegetable oil, sesame oil, safflower oil, avocado oil, glycerine, propylene glycol, sorbitol, $C_{12}-C_{16}$ alcohol benzoates, cyclomethicone, dimethicone, cocoa butter, vitamin E acetate, squalane, sodium pyrolidone carboxylic acid, methyl glucose ether, panthenol, melanin, octyl isononanoate (OIN), octyl dodecyl neopentanoate (e.g. Elefac I-205), isohexadecane (e.g. Permethyl 101 A), hydrogenated vegetable oil (e.g. Vegepure). Other suitable oils isopropyl myristate, triglycerides, and various silicones including dimethicones and cyclomethicones, etc. Additionally, hydrocarbon oils (e.g., pentane, hexane and $C_7-C_{22}$ hydrocarbons) are suitable for the instant invention.

Other oils include corn oil, cotton seed oil, tallow, lard, olive oil, palm kernel oil, rapeseed oil, safflower seed oil, sunflower seed oil, olive oil, sesame seed oil, coconut oil, arachis oil, castor oil and acetylated lanolin alcohols. Also useful are oils and waxes, such as Evening Primrose oil, beeswax, ozokerite wax, and paraffin wax.

Non-volatile, nonionic silicone materials suitable for the present invention are selected from the group comprising polyalkyl siloxanes, polyaryl siloxanes, polyalkylaryl siloxanes, polyether siloxane copolymers and mixtures thereof. The nonvolatile polyalkyl siloxane fluids that may be used include, for example, polydimethylsiloxanes, available, for example, from General Electric Company as SF 1075 methyl phenyl fluid or from Dow Corning as 556 Cosmetic Grade Fluid. The polyether siloxane copolymers that may be used include, for example, a polypropylene oxide modified dimethylpolysiloxane (E.g., Dow Corning DC-1248) although ethylene oxide or mixtures of ethylene oxide and propylene oxide may also be used.

Silicone fluids hereof also include polyalkyl or polyaryl siloxanes with the following general formula:

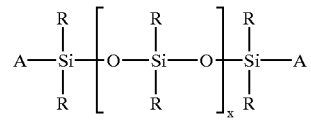

wherein R is alkyl or aryl, and x is an integer form about 7 to about 8,000. "A" represents groups which block the ends of the silicone chains.

Suitable A groups include methyl, methoxy, ethoxy, propoxy, and aryloxy. The two R groups on the silicone atom may represent the same or different groups. Preferably, the two R groups represent the same group. Suitable R groups include, for example, methyl, ethyl, propyl, phenyl, methylphenyl and phenylmethyl. The somewhat preferred silicones are polydiemethyl siloxane, polydiethyl siloxane and polymethylphenyl siloxane. The silicone material for use in compositions of the invention can be any silicone material of the required viscosity. For example, polyalkyl siloxanes, polyalkylaryl siloxanes, aminofunctional silicones, polydiorganosiloxanes or mixtures thereof may be used.

Silicone gums i.e., non volatile silicones, may be used as the'silicone materials. For the purpose of the present invention, the term silicone gum denotes polydiorganosiloxanes having a molecular weight of 200,000 to 2,000,000. Examples of suitable silicone gums are for example described in U.S. Pat. No. 4,152,416. Specific examples of suitable silicone gums are polydimethyl or polydiphenyl siloxane polymers.

Such silicone materials for use in the compositions of the invention have a viscosity of $10^4$ to $10^9$ mpa.s at 25° C, more preferably from $5\times10^4$ to $5\times10^8$, most preferably from $10^5$ to $5\times10^7$ mPa.s. A suitable method for measuring the viscosity is by means of a glass capillary viscometer (of Dow Corning CTM 0004), or by a Brookfields synchrolectric viscometer (of Dow Corning CTM 0050).

In certain embodiments of the invention, the oil phases of compositions also comprise a carrier or diluent material for the high viscosity, non-volatile silicone material. Often, high viscosity silicone materials are supplied as a dispersion in a carrier or diluent material, for example as a 5–25% by weight dispersion of the high viscosity silicone in cyclomethicone, linear dimethicone and/or isoparaffin. Alternatively or additionally the oil phase may comprise further diluents such as for example low viscosity silicones (having a viscosity of say between 0.1 to 1,000 mpa.s, more preferably o.5 to 500 mPa.s most preferably 0.65–100), liquid paraffins or methicones and other solvents such as $C_{10}$ to $C_{12}$ isoparaffins such as Isopar L (Esso), polyisobutene such as polysynlane (Nippon Oils and Fats), squalane such as Squalene (J. G. Marthens), branched chain hydrocarbons e.g., Permethyl 99A (Presperse), branched chain light paraffin oils such as Lytol (Witco) or WM1 (BP), mineral oil such as Marchol 82 (Esso) or Carnation Oil (Witco), long chain alkyl alkanoic esters such as decyl oleate (e.g., Cetiol V ex Henkel), isopropyl myristate (e.g., Estol 1514 ex Unichema) and glyceryl tri(2-ethyl hexanoate) e.g., Myritol CTEG ex Henkel).

In preferred embodiments, the silicone oil will comprise a cyclomethicone or dimethicone. Generally such silicones may be represented by the formula:

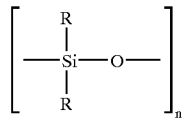

wherein R is a 1 to 3 carbon alkyl group, n is a number from 3 to 10, preferably from 3 to 7, and the unsatisfied valences on the oxygen and silicon atoms at the ends of the chain may be joined to one another to form a cyclic structure. Suitable volatile silicones are, for example, U.C.C. Y-7207, sold by Union Carbide Corporation in which each R is methyl and which typically comprises by weight 99.4% tetramer, 0.6% trimer and traces of the pentamer and hexamer; SWS-03314, sold by SWS Silicones, a Division of Stauffer Chemical Company, in which R is methyl and which is substantially all tetramer; and Dow Corning 344 fluid, sold by Dow Corning, Inc., in which R is methyl and which typically comprises by weight about 88% tetramer, about 11.8% pentamer and traces of trimer and hexamer.

The oils that may be used in the emulsions also include petroleum distillates, solvents and hydrocarbons such as, for example, mineral spirits, kerosene, terpenes, and glycol ethers.

Solid Particulate Mater Ingredients

Solid particulate matter useful in the instant invention includes solid materials listed below along with, for example, inorganic sunscreens, powders, pigments, abrasives, coal tar, anti dandruff agents or a mixture thereof. Suitable anti-dandruff agents are zinc pyrithone, selenium sulfide, sulfur, zinc omadine, piroctone olamine and mixtures thereof.

Sunscreen Ingredients Cosmetic chemists have devoted much effort towards developing methods and compositions for improving the SPF ("sun protection factor") efficiency of sunscreen vehicles, i.e. delivering higher sun protection factor with a given amount of sunscreening agent.

The sunscreen component for use in the inventive compositions may be a single sunscreen or a mixture of more than one sunscreen. The sunscreens may be organic or inorganic sunscreens, or a combination of organic and inorganic sunscreens. Suitable sunscreens are those capable of blocking, scattering, absorbing or reflecting UV radiation. Inorganic sunscreens, often referred to as physical sunscreens, typically scatter, reflect and absorb UV radiation while organic sunscreens generally absorb UV radiation. Representative sunscreen components capable of protecting human skin from the harmful effects of UV-A and UV-B radiation are set forth below in Table A.

TABLE A

| CTFA Name | FDA Name / Chemical name |
|---|---|
| Benzophenone-3 | Oxybenzone/2-Hydroxy-4-methoxy benzophenone |
| Octylmethoxycinnamate | 2-Ethylhexyl-p-methoxy cinnamate |
| Benzophenone-4 | Sulisobenzone/2-Hydroxy-4-methoxy benzophenone-5-sulfonic acid |
| Octylsalicylate | 2-Ethylhexyl salicylate |
| Triethanolamine salicylate | Triethanolamine o-hydroxybenzoate |
| Glyceryl PABA | Glyceryl p-aminobenzoate |
| Padimate O | Octyldimethyl p-aminobenzoate |
| Homosalate | Homomenthyl salicylate |
| PABA | p-Aminobenzoic acid |
| Padimate A | Amyldimethyl PABA |
| Benzophenone-8 | Dioxybenzone |
| Octocrylene | 2-Ethyl-hexyl-2-cyano-3,3-diphenyl-acrylate |
| Phenyl Benzimidazole sulfonic acid | 2-Phenylbenzimidazole-5-sulfonic acid |
| Titanium dioxide | Titanium dioxide |
| Melanin coated titanium dioxide | |
| Zinc oxide | Zinc oxide |
| Avobenzone | Butyldibenzomethane |

Preferred sunscreens and sunscreen combinations are ethyl hexyl-p-methoxy-cinnamate (commerically available from Givaudan as Parsol MCX), Benzophenone-3 (Oxybenzone commercially available from Haarmann & Reimer), 2-phenylbenzimidazole-5-sulfonic acid (commercially available as Eusolex 232 from Rona), and octyidimethyl p-amino benzoic acid (octyl dimethyl PABA commercially available from Haarmann & Reimer).

Preferred inorganic (physical) sunscreens include appropriately sized particles of micronized titanium dioxide ($TiO_2$) and zinc oxide (ZnO). In addition, these particles may have various surface treatments to render the surface non-reactive and/or hydrophobic. Inorganic sunscreens may be added to the inventive formulations on a dry basis or as predispersed slurries.

In the case of predispersed slurries, well dispersed slures are prefered. Representative non-limiting examples of currently preferred inorganic sunscreens include a slurry of 40% by weight of aluminum stearate coated micronized titanium dioxide in Octyl dodecylneopentanoate (commercially available as TiOSperse I from Collaborative Laboratories); a slurry containing 40% by weight of a mixture of $TiO_2$ and aluminum stearate in caprylic/capric triglyceride (commercially available as TiOSperse GT from Collaborative Laboratories); a 40% slurry of glycerol coated $TiO_2$ in butylene glycol and glycerin (commercially available as TiOSperse BUG/Gly from Collaborative Laboratories); melanin coated $TiO_2$ (commercially available from MelCo); ultrafine silicone coated $TiO_2$ (commercially available as UV-Titan from Presperse, Inc.); Dimethicone coated ZnO (commercially available as Z-cote HP1 from SunSmart, Inc.); a 60% $TiO_2$, aluminum stearate, an trifluoromethyl-$C_{1-4}$ alkyldimethicone in octyl dodecylneopentanoate (commercially available as ON60TA from Kobo Products, Inc.); and a 40% $TiO_2$ slurry in octyl palmitate (commercially available as Tioveil OP from Tioxide Specialties, Ltd.).

Auxiliary Co-Emulsifiers

Although not necessary and somewhat less preferred, emulsions of the instant invention can contain optional auxiliary co-emulsifiers. These auxiliary emulsifiers typically include a low HLB materials such as glycerol esters including glycerol monostearate (GMS) and glycerol monooleate (GMO), ethylene glycol distearate (EGDS), PEG esters such as polyethylene glycol monostearate, polyglyceryl esters such as polyglyceryl-10-decaoleate (e.g.Drewpol), and silicone emulsifiers such as polysiloxane based water-in-oil emulsifiers (e.g. Abil EM-90). These auxiliary low HLB emulsifiers have HLB's of from about 1 to 6, and preferably from about 1.5 to about 3.8.

Auxiliary Nonionic Surfactants Although it is preferable that the inventive compositions (and methods to produce such compositions) are free of nonionic surfactants, the inventive compositions may optionally contain auxiliary nonionic surfactants. The auxiliary nonionic surfactants that may be utilized according to the present invention are well known to the art and are described below in a representative manner.

Suitable auxiliary nonionic surfactants in accordance with the present invention are generally disclosed at column, 13 line 14 through column 16, line 6 of U.S. Pat. No. 3,929,678, the disclosure of which is incorporated herein by reference in its entirety. Generally, the auxiliary nonionic surfactant is selected from the group comprising polyoxyethyleneated alkylphenols, polyoxyethyleneated straight chain alcohols, polyoxyethyleneated branched chain alcohols, polyoxyethyleneated polyoxypropylene glycols, polyoxyethyleneated mercaptans, fatty acid esters, glyceryl fatty acid esters, polyglyceryl fatty acid esters, propylene glycol esters, sorbitol esters, polyoxyethyleneated sorbitol esters, polyoxyethylene glycol esters, polyoxyethyleneated fatty acid esters, primary alkanolamides, ethoxylated primary alkanolamides, secondary alkanolamides, ethoxylated secondary alkanolamides, tertiary acetylenic glycols, polyoxyethyleneated silicones, N-alkylpyrrolidones, alkylpolyglycosides, alkylpolylsaccharides, EO-PO blockpolymers, polyhydroxy fatty acid amides, amine oxides and mixtures thereof. Further, exemplary, non-limiting classes of useful auxiliary nonionic surfactants are listed below:

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to 12 carbon atoms in either a straight or branched chain configuration with the alkylene oxide. In a preferred embodiment, the ethylene oxide is present in an amount equal to from about 1 to about 25 moles of ethylene oxide per mole of alkyl phenol. Commercially available auxiliary nonionic surfactants of this type include Igepal® C.O-630, marketed by the GAF Corporation; and Triton® X-45, X-114, X-100 and X-102, all marketed by the Rohm and Haas Company.

2. The condensation products of aliphatic alcohols with from about 1 to about 25 moles of ethylene oxide. The alkyl chain of the aliphatic alcohol can either be straight or branched, primary or secondary, and generally contain from about 8 to about 22 carbon atoms. Particularly preferred auxiliary nonionics are the condensation products of alcohols having an alkyl group containing from about 6 to about 11 carbon atoms with from about 2 to about 10 moles of ethylene oxide per mole of alcohol. Examples of commercially available auxiliary nonionic surfactants of this type include Tergitol® 15-S-9 (the condensation products of $C_{11}$–$C_{15}$ linear alcohol with 9 moles of ethylene oxide), Tergitol® 24-L-6 NMW (the condensation products of $C_{12}$–$C_{14}$ primary alcohol with 6 moles of ethylene oxide with a narrow molecular weight distribution), both marketed by Union Carbide Corporation; Neodol® 91-8 (the condensation product of $C_9$–$C_{11}$ linear alcohol with 8 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 91-6 (the condensation product of $C_9$–$C_{11}$ linear alcohol with 6 moles of ethylene oxide), marketed by Shell Chemical Company, and Kyro® EOB (the condensation product of $C_{13}$–$C_{15}$ linear alcohol with 9 moles of ethylene oxide), marketed by the Procter and Gamble Company.

3. The condensation products of ethylene oxide with a hydrophobic base formed by the condensation of propylene oxide with propylene glycol. The hydrophobic portion of these compounds preferably has a molecular weight of from about 1500 to about 1880 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Alkylpolysaccharides disclosed in U.S. Pat. No. 4,565,647, Lenado, issued Jan. 21, 1986, incorporated herein by reference, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally, the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

6. An ethyl ester ethoxylate and/or alkoxylate such as those described in U.S. Pat. No. 5,220,046, incorporated herein by reference. These material may be prepared according to the procedure set forth in Japanese Kokai patent application No. HEI 5 [1993]-222396. For example, they may be prepared by a one-step condensation reaction between an alkyl ester and an alkylene oxide in the, present of a catalytic amount of magnesium together with another ion selected from the group of $Al^{+3}$, $Ga^{+3}$, $In^{+3}$, $Co^{+3}$, $Sc^{+3}$, $La^{+3}$ and $Mn^{+3}$. Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched, containing from about 8 to about 18, preferably from about 12 to about 14 carbon atoms; n is 2 or 3, preferably 2; t is from about 0 to about 10, preferably 0; and x is from about 1.3 to about 10, preferably from about 1.3 to 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glucosyl units can then be attached between their 1-position and the preceding glycosyl units 2-, 3-, 4- and/or 6-position, preferably predominately the 2-position.

7. Other auxiliary nonionic surfactants include alkoxylated mono- and diglycerides of fatty acids. Preferred are ethoxylated and/or propoxylated glycerides of fatty acids having from 6–40 carbon atoms. Suitable alkoxylated mono- and diglycerides of such acids are commercially available from Witco Corporation. Examples of such auxiliary nonionic surfactants include Varonic LI-63 (PEG-30 Glyceryl Cocoate, Witco), Varonic LI-67 (PEG-80 Glyceryl Cocoate, Witco), Varonic LI-67, 75% (PEG-80 Glyceryl Cocoate, Witco), Varonic LI-42 (PEG-20 Glyceryl Tallowate, Witco), Varonic LI-48 (PEG-80 Glyceryl Tallowate, Witco), and Varonic LI-420, 70% (PEG-200 Glyceryl Tallowate, Witco).

8. Additional auxiliary nonionic surfactants are alkoxylated alkyl esters of fatty acids. Preferred auxiliary alkoxylated alkyl esters are ethoxylated and/or propoxylated methyl esters of fatty acids having from 8–40 carbon atoms. Suitable auxiliary alkoxylated methyl esters of such acids are commercially available from Lion Corporation. Examples of such auxiliary nonionic surfactants include $RCO_2(CH_2CH_2O)_nCH_3$ where R is $C_{12}$, and n is about 10.9 (commercially available from Lion Corporation, Japan, as LC-110M), and $RCO_2(CH_2CH_2O)_nCH_3$ where R is $C_{12}$, and n is about 14.6 (commercially available from Lion Corporation, Japan, as LC-150M-92).

Optional Ingredients

The following optional ingredients can be present in various quantities. The ternary surfactant blends may be formulated with optional components, such as fragrances, emollient, solvents, humectants, optical brightners, thickeners, powders, viscosity modifiers, hydrotropes, preservatives, bluing agents, and dyes, to produce a wide variety of end use products.

Generally, a wide variety of functional materials can optionally be present in the invention emulsions/suspensions and/or finished formulations which contain the emulsions/suspensions. Non-limiting examples of such option functional materials, include absorbenst, algicides, antimicrobials, bactericides, disinfectants, fungicides, anticaking agents, antioxidants, antiperspirants, anitsoils, soil antiredeposition agents, antistats, binders, carriers, chelating/sequestering agents, colorants, peralescents, conditioners, corrosion inhibitors, coupling agents, hydrotropes, defoamers, detergent builders, dispersants, emollients, enzymes, flocculants, florescent whitening agents, hair fixatives, humectants, lubricants, opacifiers, plasticizers, powders, preservatives, release agents, scale inhibitors, solubilizers, solvents, stablizers, suspending agents, thickeners, waxes and polishes, as generally disclosed in *McCutcheon's Functional Materials,* (1997 North American Eddition).

Although the use of such optional components is not essential to the present invention, and may in fact be somewhat less preferred depending on the desired final formulation and end use application, suitable additional optional emollients useful in formulating with blends of the present invention include, for example, stearyl alcohol, glyceryl ricinoleate, glyceryl stearate, propane-1,2-diol, butane-1,3-diol, mink oil, cetyl alcohol, stearamidopropyl dimethylamine, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, di-n-butyl sebacate, isopropyl myristate, isopropyl palmitate, isopropyl stearate, butyl stearate, polyethylene glycol, triethylene glycol, lanolin, cocoa butter, butyl myristate, isostearic acid, palmitic acid, isopropyl linoleate, lauryl lactate, myristyl lactate, decyl oleate, and myristyl myristate, and mixtures thereof.

Although generally less preferred, optional solvents useful in formulating with blends of the present invention include, for example, ethyl alcohol, propylene glycol, water, isopropanol, castor oil, ethylene glycol monoethyl ether, diethylene glycol monobutyl ether, diethylene glycol monoethyl ether, dimethyl sulphoxide, dimethyl formamide, and tetrahydrofuran, and mixtures thereof.

Optional humectants useful in formulating with compositions of the present invention include, for example, glycerin, sorbitol, sodium 2-pyrrolidone-5-carboxylate, soluble collagen, dibutyl phthalate, propylene glycol, and gelatin, and mixtures thereof.

Optional swellable polymer thickening agents include, for example, methyl cellulose, ethyl cellulose, xanthan gum, gum arabic, gum karaya, guar gum, locust bean gum, ghatti gum, hydrolyzed starches, low molecular weight ethylene oxide polymers, low molecular weight propylene oxide polymers and mixtures thereof.

The optional pearlescent/suspending agents suitable for use in the present invention include any of several long chain acyl derivative materials or mixtures of such materials, such as long chain acyl derivatives, long chain amine oxides, and mixtures thereof, wherein such suspending/pearlescent agents are present in the composition in crystalline form. These pearlescent/suspending agents are described in U.S. Pat. No. 4,741,855, Grote and Russell, issued May 3, 1988, the disclosure of which is incorporated herein by reference in its entirety. Included are ethylene glycol esters of fatty acids having from about 16 to about 22 carbon atoms. Preferred are the ethylene glycol stearates, both mono- and distearate, but particularly the distearate containing less than about 7% of the monostearate. Other suspending agents found useful are alkanolamides, preferably with about 16 to about 18 carbon atoms. Preferred alkanolamides are stearic monoethanolamide, stearic diethanolamine, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain ester of long chain alkanol amides (e.g., stearamide DEA distearate, stearamide MEA stearate).

Additional optional pearlescent/suspending agents suitable for use in the present invention are alkyl ($C_{18}$–$C_{22}$) dimethyl amine oxides, such as stearyl dimethyl amine oxide. If the compositions contain an amine oxide or a long chain acyl derivative as a surfactant the pearlescent/suspending function could also be provided by such surfactant and additional pearlescent/suspending agents may not be needed.

Further optional pearlescent/suspending agents that can be used are long chain acyl derivatives, including, for example, N,N-dihydroxycarbyl amido benzoic acid and soluble thereof (e.g., Na and K salts), particularly N,N-di (hydrogenated) $C_{16}$, $C_{18}$ and tallow amido benzoic acid species of this family, which are commercially available from Stepan Company (Northfield, Ill., USA).

Another type of pearlescent/suspending agent which can be used in the present invention is xanthan gum. Xanthan gum is well known to those skilled in the art. For example, hair care compositions utilizing xanthan gum as a pearlescent/suspending agent for the silicone hair conditioning component are described in U.S. Pat. No. 4,788,066, Bolich and Williams, issued Nov. 29, 1988, the disclosure of which is incorporated herein by reference in its entirety. See also, Whistler, Roy L. Editor Industrial Gums—Polysaccharides and Their Derivatives, New York: Academic Press, 1973. Xanthan gum is commercially available from Kelco, a division of Merck & Co., Inc. as Keltrol.

Combinations of long chain acyl derivatives and xanthan gum are disclosed as pearlescent/suspending agents for silicone hair conditioners in U.S. Pat. No. 4,704,272, Oh et al., issued Nov. 3, 1987, both of which are incorporated herein by referenced in their entirety, and may also be used in the present compositions. Gel formulations have high levels of pearlescent/suspending agents relative to pourable, liquid formulations which used as the primary means of imparting gel-like viscosity. Optional gelling agents suitable for use in the present invention include, for example, hydroxy ethylcellulose.

Other optional conditioning agents include sucrogylericide materials, particularly those disclosed in U.S. Pat. No. 5,705,147, issued Jan. 6, 1998 to Stepan Company, incorporated herein in its entirety.

Optional powders useful in formulating with compositions of the present invention include, for example, chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, cellulosics such as hydroxyethyl cellulose and sodium carboxymethyl cellulose, ethylene glycol monostearate, zinc or magnesium stearate, zinc oxide and magnesium oxide, and mixtures thereof. These components may also be used as thickeners in fluid or semi-fluid compositions.

Examples of other optional ingredients useful in formulating with compositions of the present invention include, for example, silicone polymers; preservatives, such as parahydroxy benzoate esters; humectants, such as butane-1,3-diol, glycerol, sorbitol, polyethylene glycol; stabilizers, such as sodium chloride or ammonium chloride; buffer systems, such as lactic acid together with a base such as sodium hydroxide; thickeners; activity enhancers; colorants; whiteners; fragrances; and bactericides, and mixtures thereof.

The compositions of the present invention may also be formulated into finished detergent formulations, in combination with optional detergent builder materials. Nearly any detergent builders known in the art can be formulated with the present blends. Examples of useful detergent builders are described in U.S. Pat. No. 4,321,165, (to Smith et al, issued Mar. 23, 1982) and U.S. Pat. No. 5,565,145 (to Watson et al., issued Oct. 15, 1996), both incorporated herein by reference. Detergent builders can optionally be included in the compositions herein to assist in controlling mineral hardness. Inorganic as well as organic builders can be used. Builders are typically used in fabric laundering compositions to assist in the removal of particulate soils. The level of builder can vary widely depending upon the end use of the composition and its desired physical form. When present in a final formulation, the compositions will typically comprise at least about 1% builder. Liquid formulations typically comprise from about 5% to about 50%, more typically about 5% to about 30%, by weight, of detergent builder. Granular finished formulations typically comprise from about 10% to about 80%, more typically from about 15% to about 50% by weight, of the detergent builder. Lower or higher levels of builder, however, also can be acceptable.

Enzymes and enzyme stabilizers can be formulated with compositions of the instant invention for a wide variety of fabric laundering purposes, including removal of protein-based, carbohydrate-based, or triglyceride-based stains, for example, and for fabric restoration. Examples of useful enzymes and enzyme stabilizers are described. in U.S. Pat. No. 5,565,145 (to Watson et al., issued Oct. 15, 1996), incorporated herein by reference. Useful enzymes include, for example, proteases, amylases, lipases, and cellulases, as well as mixtures thereof. Other types of enzymes may also be included. They may be of any suitable origin, such as vegetable, animal, bacterial, fungal and yeast origin. However, a particular enzyme choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Suitable examples of proteases are the subtilisins which are obtained from particular strains of *B. subtilis* and *B. licheniforms*. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Pat. Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Ser. No. 87303761.8, filed Apr. 28, 1987, and European Patent Application 130,756, Boft et al, published Jan. 9, 1985).

Amylases include, for example, amylases described in British Patent Specification No. 1,296,839 (Novo), RAPIDASE, International Bio-Synthetics, Inc. and TERMAMYL, Novo Industries.

Cellulases suitable for use with compositions of the present invention include both bacterial or fungal cellulase. Preferably, they will have a pH optimum of between 5 and 9.5. Suitable cellulases are disclosed in U.S. Pat. No. 4,435, 307, Barbesgoard et al, issued Mar. 6, 1984, which discloses fungal cellulase produced from Humicola insolens and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS.247.832CAREZYME (Novo) is especially useful.

Suitable lipase enzymes include those produced by microorganisms of the Pseudomonas group, such as *Pseudomonas stutzeri* ATCC 19.154, as disclosed in British Patent. 1,372, 034. See also lipases in Japanese Patent Application 53,20487, laid open to public inspection on Feb. 24, 1978. This lipase is available from Amano Pharmaceutical Co. Ltd., Nagoya, Japan, under the trade name Lipase P Amano, hereinafter referred to as Amano-P. Other commercial lipases include Amano-CES, lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Diosynth Co., The Netherlands, and lipases ex *Pseudomonas gladioli*. The LIPOLASE enzyme derived from *Humicola lanuginosa* and commercially available from Novo (see also EPO 341,947) is a preferred lipase for use herein.

A wide range of enzyme materials and means for their incorporation into synthetic detergent compositions are also disclosed in U.S. Pat. No. 3,553,139, issued Jan. 5, 1971 to McCarty et al. Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. No. 3,519,570.

The optional enzymes useful herein may be stabilized by the presence of water-soluble sources of calcium and/or magnesium ions in the finished compositions which provide such ions to the enzymes. Calcium ions are generally somewhat more effective than magnesium ions and are preferred herein if only one type of cation is being used. Additional stability can be provided by the presence of various other disclosed stabilizers, especially borate species. See Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This concentration can vary somewhat, depending on the amount of enzyme present and its response to the calcium or magnesium ions. The level of calcium or magnesium ions should be selected so that there is always some minimum level available for the enzyme, after allowing for complexation with builders, fatty acids, etc., in the final composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per liter, is often also present in the final composition due to calcium in the enzyme slurry and formula water. In solid detergent compositions the final formulation may include a sufficient quantity of a water-soluble calcium ion source to provide such amounts in the laundry liquor. In the alternative, natural water hardness may suffice.

Generally, the aforementioned levels of calcium and/or magnesium ions are sufficient to provide enzyme stability to a finished formulation. More calcium and/or magnesium ions can be added to the compositions to provide an additional measure of grease removal performance. Accordingly, final formulations prepared from the blends disclosed herein typically will comprise from about 0.05% to about 2% by weight of a water-soluble source of calcium or magnesium ions, or both. The amount of water-soluble ion can vary with the amount and type of enzyme employed in the final composition.

Final compositions detailed herein, when utilized in a finished formulation, may also optionally contain various additional stabilizers, especially borate-type stabilizers. Boric acid is preferred, although other compounds such as boric oxide, borax and other borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Bleaching agents, bleach activators, chelating agents, anti-redeposition agents, polymeric dispersing agents, optical brighteners, suds suppressors, dye transfer inhibition agents, optical brighteners, and soil release agents can be formulated with blends of the instant invention. Examples of such materials are generally described in U.S. Pat. No. 5,565,145 (to Watson et al., issued Oct. 15, 1996), incorporated herein by reference.

Various other detergent additives or adjuvants may be present in the detergent product to give it additional desired properties, either of functional or aesthetic nature. Thus, there may be included in the formulation minor amounts of soil suspending or anti-redeposition agents, e.g. polyvinyl alcohol, fatty amides, sodium carboxymethyl cellulose, hydroxy-propyl methyl cellulose; optical brighteners, e.g. cotton, amine and polyester brighteners, for example, stilbene, triazole and benzidine sulfone compositions, especially, sulfonated substituted triazinyl stilbene, sulfonated naphthotriazole stilbene, benzidine sulfone, etc., most preferred are stilbene and triazole combinations.

Bluing agents such as ultramarine blue; enzymes, preferably proteolytic enzymes, such as subtilisin, bromelin, papain, trypsin and pepsin, as well as amylase type enzymes; bactericides, e.g. tetrachlorosalicylanilide, hexachlorophene; fungicides; dyes; pigments (water dispersible); preservatives; ultraviolet absorbers; anti-yellowing agents, such as sodium carboxymethyl cellulose, complex of $C_{12}$ to $C_{22}$ alkyl alcohol with $C_{12}$ to $C_{18}$ alkylsulfate; pH modifiers and pH buffers; color safe bleaches, perfume, and anti-foam agents or suds suppressors, e.g. silicon compounds, can also be used.

In the case of final formulations, other optional ingredients include neutralizing agents, buffering agents, phase regulants, hydrotropes, polyacids, suds regulants, opacifiers, antioxidants, preservatives, bactericides, dyes, perfumes, and brighteners described in the U.S. Pat. No. 4,285,841, Barrat et al, issued Aug. 25, 1981, incorporated herein by reference. Other ingredients useful in final detergent compositions can be formulated with blends of the instant invention, including carders, processing aids, pigments, solvents for liquid formulations, solid fillers for bar compositions, sodium sulfate, sodium chloride, protein hydrolysates, cholesterol derivatives, UV absorbers, chelating agents, etc. If high sudsing is desired, suds boosters such as the $C_{10}$–$C_{16}$ alkanolamides can be incorporated into the final compositions, typically at 1%–10% levels. The $C_{10}$–$C_{14}$ monoethanol and diethanol amides illustrate a typical class of such suds boosters. If desired, soluble magnesium salts such as $MgCl_2$, $MgSO_4$, and the like, can be added at levels of, typically, 0.1%–2%, to provide additional suds and to enhance grease removal performance to a final formulation.

Additionally, the compositions may optionally contain non-conventional surfactants, such as fluorosurfactants, gemini surfactants and polymeric cationic and polymeric anionic surfactants. The emulsification systems of the invention also comprise polysiloxane polyalkyl polyether copolymers, i.e., silicone glycol surfactants which are also known as copolyols. The amount of silicone glycol surfactant is preferably about 0.5 to 15% by weight. A more preferable amount of the silicone glycol surfactant is about 0.5–5% of the composition.

Suitable silicone surfactants are for example high molecular weight polymers of dimethyl polysiloxane with polyoxyethylene and/or polyoxypropylene side chains, having a molecular weight of from 10,000 to 50,000 and having the structure:

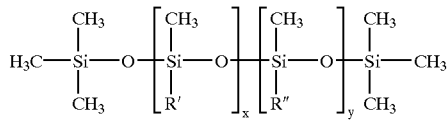

wherein the groups R' are each chosen from —H, $C_{1-18}$ alkyl and R" is —[$CH_2CH_2O$]$_a$[$CH_2(CH_2)CHO$]$_b$H, in which a has a value of from 9 to 115, b has a value of from 0 to 50, x has a value of from 133 to 673, y has a value of from 25 to 0.25. Preferably, the polymer is an alkoxylated polydimethyl polymer in which: a has a value of from 10 to 114, b has a value of from 0 to 49, x has a value of from 388 to 402, y has a value of from 15 to 0.75, M the group R" having a molecular weight of from 1000 to 5000. A more preferred alkoxylated dimethyl polysiloxane polymer is one in which: a has the value 14, b has the value 13, x has the value 249, y has the value 1.25. A particularly preferred copolyol is cetyl dimethicone copolyol, available from T. H. Goldschmidt as Abil® EM-90.

Blends of the present invention are prepared from readily available, economical raw materials, and generally their preparation does not require any special handling or equipment. The blends may be prepared in a batch mode or a continuous mode.

Suitable preservatives are selected from the group comprising benzyl alcohol, methyl paraben, propyl paraben and imidazolidinyl urea.

Suitable thickeners and viscosity modifiers are selected from the group comprising diethanolamides of long chain fatty acids (e.g., PEG-3 lauramide), block polymers of ethylene oxide and propylene oxide such as Pluronic® F88 offered by BASF, Wyandotte, sodium chloride, sodium sulfate, ammonium xylene sulfonate, ethyl alcohol and polyhydridic alcohols such as, for example, propylene glycol and polyvinyl alcohol.

Suitable gelling agents include, for example, hydroxyethyl cellulose.

Suitable pH adjusting agents are selected from the group comprising citric acid, succinic acid, phosphoric acid, sodium hydroxide, sodiumcarbonate, etc.

Suitable sequestering agents include, for example, disodium ethylenediamine tetraacetate.

The compositions of the present invention typically contain water as the solvent; however, other solvents may optionally be employed, either alone or in combination with water. Low molecular weight primary or secondary alcohols, exemplified by methanol, ethanol, propanol, and isopropanol, are suitable optional solvents. Monohydric alcohols are preferred optional solvents, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from about 5 to about 90 percent, typically from about 10 to about 50 percent by weight of water and/or optional solvent.

While pH is of secondary significance herein, the compositions of the present invention typically are prepared having a pH of between about 2 and about 10, preferably between about 5 and about 8. Techniques for controlling pH at recommended usage levels include the use of buffers, alkalis, acids, etc., and are well known to those skilled in the art. Suitable materials for adjusting the pH of these compositions include triethanolamine, diethanolamine, sodium carbonate, sodium bicarbonate, and the like.

The ternary surfactant emulsification system of this invention, in addition to emulsifying oils and suspending particulate mater, may also by itself be formulated into commercially useful products. Additionally, the ternary surfactant blends may be processed into a variety of forms such as, for example, liquids, solutions, solids, powders, flakes, semi-solids, gels, "ringing" gels, G-phase liquids/pastes, hexagonal liquid crystal phases, or thick non-flowable pastes. The ternary surfactant blends may be spray dried, flaked, or extruded. Although not critical to the present invention, the blends may be prepared "neat" or in a conventional solvent such as water, low molecular weight alcohol or hydrocarbon, or a mixture thereof, to produce a solution of the ternary surfactant blend. The present invention encompasses ternary surfactant systems in dry form and as aqueous solutions. Ternary surfactant blends in concentrations up to 100 percent by weight may be isolated by drying a solution of the blend. Conversely, ternary surfactant blend solutions may be prepared by dissolving a solid form of the blend in water, low molecular weight alcohol, low molecular weight glycol, or mixtures thereof.

One skilled in the art will recognize that modifications may be made in the present invention without deviating from the spirit or scope of the invention. The invention is illustrated further by the following examples, which are not to be construed as limiting the invention or scope of the specific procedures or compositions described herein. All documents, e.g., patents and journal articles, cited above or below are hereby incorporated by reference in their entirety.

As used in the Examples appearing below, the following designations, symbols, terms and abbreviations have the indicated meanings:

| Material | Definition |
|---|---|
| ALPHA STEP ®MC-48 | Sodium alphasulfo methyl $C_{12-18}$ ester (and) disodium alphasulfo $C_{12-18\ fatty}$ acid salt (commercially available from Stepan Company, Northfield Illinois) |
| POLYSTEP ® B-25 | Sodium decyl sulfate (commercially available from Stepan Company, Northfield Illinois) |

-continued

| Material | Definition |
|---|---|
| BIOTERGE ® PAS-8S | Sodium octyl sulfonate (commercially available from Stepan Company, Northfield Illinois) |
| STEOL ® CS-370 | Sodium laureth sulfate (3EO) (commercially available from Stepan Company, Northfield Illinois) |
| STEOL ® CS-460 | Ammonium laureth sulfate (3EO) (commercially available from Stepan Company, Northfield Illinois) |
| STEPANOL ® WA-EXTRA | Sodium lauryl sulfate (commercially available from Stepan Company, Northfield Illinois) |
| BIOTERGE ® AS-40 | Sodium C14–16 olefin sulfonate (commercially available from Stepan Company, Northfield Illinois) |
| QC8 | Octyltrimethylammonium chloride |
| CETAC ® 30 | Cetyltrimethylammonium chloride (commercially available from Stepan Company, Northfield Illinois) |
| BTC ® 65NF | Dimethylbenzylammonium chloride (commercially available from Stepan Company, Northfield Illinois) |
| AMMONYX ® GA | Dipalmitoylethylhydroxyethylmonium methosulfate (commercially available from Stepan Company, Northfield Illinois) |
| STEPAN MILD ® RM1 | Sodium Stearyl Phtalamate (commercially available from Stepan Company, Northfield Illinois) |
| AMMONYX ® LO | Lauramine oxide (commercially available from Stepan Company, Northfield Illinois) |
| AMPHOSOL ® CA | Cocamidopropyl betaine (commercially available from Stepan Company, Northfieid Illinois) |
| ELEFAC I-205 | Octyldodecyl neopentanoate |
| MICRO LA-20 | Titanium dioxide 80% |
| CARBOPOL ULTREZ 10 | Polymer-acrylic acid backbones and polyalkenylpolyether crosslinking agents (commercially available from B.F. Goodrich) |
| ELEFAC I-205 | Octyldodecyl neopentanoate (commercially available from Bernel Chemical Comp. Inc.) |
| MICRO LA-20 | Titanium dioxide 80% (commercially available from Grant Industries) |
| KESSCO ® IPP | Isopropylpalmitate (commercially available from Stepan Company, Northfield Illinois) |
| SILICONE DC-200 | Silicone oil (commercially available from Dow Corning) |

One skilled in the art will recognize that modifications may be made in the present invention without deviating from the spirit or scope of the invention. The invention is illustrated further by the following examples, which are not to be construed as limiting the invention or scope of the specific procedures or compositions described herein.

In the following examples, all amounts are stated in percent by weight of active material unless indicated otherwise.

EXAMPLE 1
Concentrated o/w Emulsions

Several concentrated o/w emulsions as shown in Table 1 were prepared using the following procedure. Premix with agitation, at about 25° C., the anionic surfactant, cationic surfactant, and bridging surfactant at equimolar ratios. Add the water to the surfactant mixture and mixing well with agitation. Add the oil phase, mix well with agitation at about 25° C. for 30 minutes. As can be seen by the results reported in Table 1, stable concentrated o/w emulsions are formed using different anionic-cationic-bridge systems and different oils (silicone, mineral oils).

TABLE 1

| O/W Emulsions 1, 2, 3 | | #1 % active | | #2 % active | | #3 % active |
|---|---|---|---|---|---|---|
| Anionic surfactant | WA-extra | 2.08 | WA-extra | 2.08 | WA-extra | 2.38 |
| Cationic surfactant | QC8 | 1.43 | QC8 | 1.43 | QC8 | 1.64 |
| Bridge surfactant | AMPHCA | 2.49 | AMPHCA | 2.49 | AMXLO | 1.98 |
| Total CAN system* | | 6 | | 6 | | 6 |
| silicone DC-200 | | 70 | | | | 70 |
| mineral oil | | | | 70 | | |
| water | | qs 100 | | qs 100 | | qs 100 |
| stability at 25° C., 43° C. and 50° C. at 30 days | | stable | | stable | | stable |

| O/W Emulsions 4,5,6 | | #4 % active | | #5 % active | | #6 % active |
|---|---|---|---|---|---|---|
| Anionic surfactant | AS-40 | 2.14 | B25 | 1.91 | PAS-8S | 1.79 |
| Cationic surfactant | QC8 | 1.41 | QC8 | 1.49 | CETAC | 2.36 |
| Bridge surfactant | AMPHCA | 2.45 | AMPHCA | 2.6 | AMXLO | 1.85 |
| Total CAN system* | | 6 | | | | |
| mineral oil | | 70 | | 70 | | 70 |
| water | | qs 100 | | qs 100 | | qs 100 |
| stability at 25° C., 43° C. and 50° C. at 30 days | | stable | | stable | | stable |

| O/W Emulsion 7 | | #7 % active |
|---|---|---|
| Anionic surfactant | MC48 | 2.24 |
| Cationic surfactant | QC8 | 1.37 |
| Bridge surfactant | AMPHCA | 2.39 |
| Total CAN system* | | 6 |

TABLE 1-continued

| | |
|---|---|
| mineral oil | 70 |
| water | qs 100 |
| stability at 25° C., 43° C. and 50° C. at 30 days | stable |

*CAN system = cationic, anionic, nonionic or bridge surfactants

EXAMPLE 2

As shown in TABLE 2, a stable o/w emulsion is formed when an anionic, cationic, bridge surfactant system is used. Comparative unstable emulsions (emulsions 9–14) are obtained when individual surfactants or any of the two components surfactant system is used. It is critical to use the three components to form a stable emulsion. All emulsions shown in Table 2 below were prepared using the procedure described in Example 1 above.

TABLE 2

| | | #8 | Comp. #9 | Comp. #10 | Comp. #11 | Comp. #12 | Comp. #13 | Comp. #14 |
|---|---|---|---|---|---|---|---|---|
| O/W Emulsions 8, and comparative 9, 10, 11, 12, 13, 14 | | % active | % active | % active | % active | % active | % active | % active |
| Anionic surfactant | WA-extra | 2.08 | 6 | | | 3.55 | 2.73 | |
| Cationic surfactant | QC8 | 1.43 | | 6 | | 2.45 | | 2.19 |
| Bridge surfactant | AMPHCA | 2.49 | | | 6 | | 3.27 | 3.81 |
| Total CAN system* | | 6 | | | | 6 | 6 | 6 |
| silicone DC-200 | | 70 | 70 | 70 | 70 | 70 | 70 | 70 |
| water | | qs 100 | qs 100 | qs 100 | qs 100 | qs 100 | qs 100 | qs 100 |
| stability at 25° C., 43° C. and 50° C. at 30 days | | stable | unstable | unstable | unstable | unstable | unstable | unstable |

*CAN system = cationic, anionic, nonionic or bridge surfactants

EXAMPLE 3

Various concentrated o/w emulsions were prepared using the same procedure as detailed in Example 1. As shown in Table 3 the stability of the concentrated emulsion was maintained over a wide pH range (2.5–10.5).

TABLE 3

| | | #15 | #16 | #17 | #18 | #19 |
|---|---|---|---|---|---|---|
| O/W Emulsions 15, 16, 17, 18, 19 | | % active | % active | % active | % active | % active |
| Anionic surfactant | WA-extra | 2.08 | 2.08 | 2.08 | 2.08 | 2.08 |
| Cationic surfactant | QC8 | 1.43 | 1.43 | 1.43 | 1.43 | 1.43 |
| Bridge surfactant | AMPHCA | 2.49 | 2.49 | 2.49 | 2.49 | 2.49 |
| Total CAN system | | 6 | 6 | 6 | 6 | 6 |
| silicone DC-200 | | 70 | 70 | 70 | 70 | 70 |
| water | | qs 100 | qs 100 | qs 100 | qs 100 | qs 100 |
| pH | | 7.8 | 2.5 | 4 | 6 | 10.3 |
| stability at 25° C., 43° C. and 50° C. at 30 days | | stable | stable | stable | stable | stable |

*CAN system = cationic, anionic, nonionic or bridge surfactants

EXAMPLE 4
Dilutable Concentrated Emulsions

As shown in TABLE 4 the results indicate that dilutable emulsions prepared from the concentrated emulsions at room temperature are both obtainable and stable. The emulsions were prepared using the following procedure: Premix the anionic, cationic, bridge system at about 25° C. with agitation and at equimolar ratios. Add the water to the surfactant mixture with agitation. Add the oil phase and mix well with agitation at 25° C. for 30 minutes. After formation of the concentrated emulsion, the rheology modifier is dispersed in the required amount of water for the dilution, with agitation for about 5 minutes. Add the concentrated emulsion to this rheology/water phase along with concurrent addition of the triethanoamine until the desired pH is reached, with agitation at about 25° C. for 30 minutes. The results below show that the concentrated emulsions (70% oil) are readily dilutable and stable upon dilution.

TABLE 4

| O/W Emulsions 20,21 | | #20 % active | | #21 % active |
|---|---|---|---|---|
| Anionic surfactant | STCS460 | 2.54 | STCS460 | 0.54 |
| Cationic surfactant | BTC65NF | 2.02 | BTC65NF | 0.43 |
| Bridge surfactant | AMXLO | 1.44 | AMXLO | 0.31 |
| Total CAN system | | 6 | | 1.28 |
| silicone DC-200 | | 70 | | 15 |
| Ultrez-10 | | 0 | | 0.3 |
| TEA to pH | | 7 | | 6.3 |
| water | | qs100 | | qs100 |
| stability at 25° C., 43° C. and 50° C. at 30 days | | stable | | stable |

*CAN system = cationic, anionic, nonionic or bridge surfactants

EXAMPLE 5

Several o/w emulsions with lower percentage of oil were prepared at about 25° C. as shown in TABLE 5 using the following procedure: Premix the anionic, cationic, bridge surfactants at about 25° C. at equimolar ratio (see the weight ratio in the table). Add the water to the surfactant mixture with agitation. Disperse the Carbopol Ultrez 10 in the aqueous layer with agitation. Add the oil phase to the Carbopol Ultrez 10/aqueous phase and mix well with agitation at 25° C. for 5 minutes. Add the triethanolamine with agitation to the required pH (greater than 5). Continue the mixing for approximately 45 minutes at 25° C. The results indicate the successful formation of stable o/w emulsions using different anioncs, cationics or bridging systems. The results indicate that it is possible to emulsify a variety of different oils (silicone oil, mineral oil, cosmetic esters) at varying concentrations of such oils.

TABLE 5

| O/W Emulsions 22, 23, 24 | | #22 % active | | #23 % active | | #24 % active |
|---|---|---|---|---|---|---|
| Anionic surfactant | STCS460 | 0.64 | STCS460 | 0.64 | STCS460 | 0.64 |
| Cationic surfactant | BTC65NF | 0.5 | BTC65NF | 0.5 | BTC65NF | 0.5 |
| Bridge surfactant | AMXLO | 0.36 | AMXLO | 0.36 | AMXLO | 0.36 |
| Total CAN system | | 1.5 | | 1.5 | | 1.5 |
| silicone DC-200 | | | | 15 | | |
| mineral oil | | | | | | 15 |
| IPP | | 15 | | | | |
| Ultrez-10 | | 0.3 | | 0.3 | | 0.3 |
| TEA to pH | | 7 | | 7.4 | | 6.5 |
| water | | qs 100 | | qs 100 | | qs 100 |
| stability at 25° C., 43° C. and 50° C. at 30 days | | stable | | stable | | stable |

| O/W Emulsions 25, 26, 27, 28 | | #25 % active | | #26 % active | | #27 % active | | #28 % active |
|---|---|---|---|---|---|---|---|---|
| Anionic surfactant | STCS460 | 0.66 | STCS460 | 0.59 | STCS460 | 0.57 | AS-40 | 0.46 |
| Cationic surfactant | Cetac 30 | 0.47 | Cetac 30 | 0.43 | BTC65NF | 0.46 | BTC65NF | 0.51 |
| Bridge surfactant | AMXLO | 0.37 | AMPHCA | 0.48 | AMPHCA | 0.47 | AMPHCA | 0.53 |
| Total CAN system | | 1.5 | | 1.5 | | 1.5 | | 1.5 |
| IPP | | 15 | | 15 | | 15 | | 15 |
| Ultrez-10 | | 0.3 | | 0.3 | | 0.3 | | 0.3 |
| pH | | 7 | | 6.7 | | 5.6 | | 7 |
| stability at 25° C., 43° C. and 50° C. at 30 days | | stable | | stable | | stable | | stable |

| O/W Emulsions 29, 30, 31 | | #29 % active | | #30 % active | | #31 % active |
|---|---|---|---|---|---|---|
| Anionic surfactant | WA-extra | 0.87 | STCS460 | 0.64 | STCS460 | 0.85 |
| Cationic surfactant | QC8 | 0.59 | BTC65NF | 0.5 | BTC65NF | 0.67 |
| Bridge surfactant | AMPHCA | 1.04 | AMXLO | 0.36 | AMXLO | 0.48 |
| CAN system | | 2.5 | | 1.5 | | 2 |
| IPP | | 20 | | 15 | | 15 |
| Ultrez-10 | | 0.5 | | 0.3 | | 0.3 |
| TEA to pH | | 5.5 | | 7 | | 7 |
| water | | qs 100 | | qs 100 | | qs 100 |
| stability at 25° C., 43° C. and 50° C. at 30 days | | stable | | stable | | stable |

| O/W Emulsions 32, 33 | | #32 % active | | #33 % active |
|---|---|---|---|---|
| Anionic surfactant | WA-extra | 0.68 | WA-extra | 0.71 |
| Cationic surfactant | QC8 | 0.46 | QC8 | 0.49 |
| Bridge surfactant | AMXLO | 0.56 | AMXLO | 0.6 |
| Total CAN system | | 1.7 | | 1.8 |
| silicone DC-200 | | 50 | | |
| mineral oil | | | | 50 |
| Ultrez-10 | | 0.3 | | 0.2 |
| TEA to pH | | 7 | | 7 |
| water | | qs 100 | | qs 100 |
| stability at 25° C., 43° C. and 50° C. at 30 days | | stable | | stable |

*CAN system = cationic, anionic, nonionic or bridge surfactants

EXAMPLE 6

As shown in TABLE 6 a stable o/w emulsion is obtained without the premixing of the three anionic, cationic and nonionic/bridging surfactant components. The same procedure was used as per Example #5 above, the only difference was the anionic, cationic, bridge surfactants, along with the water, were individually added to the oil phase without the premixing. The results further indicate stable o/w emulsions using an anionic, cationic, bridge system as an emulsifier. Unstable emulsions are obtained when only the anionic and the cationic surfactants are used. The bridging surfactant serves to stabilize the emulsion.

TABLE 6

| O/W Emulsions 34, 35, 36 | | #34 % active | | Comp. #35 % active | | Comp. #36 % active |
|---|---|---|---|---|---|---|
| Anionic surfactant | STCS460 | 0.64 | STCS460 | 0.64 | STCS460 | 0.84 |
| Cationic surfactant | BTC65NF | 0.5 | BTC65NF | 0.5 | BTC65NF | 0.66 |

TABLE 6-continued

| O/W Emulsions 34,35,36 | | #34 % active | Comp. #35 % active | Comp. #36 % active |
|---|---|---|---|---|
| Bridge surfactant | AMXLO | 0.36 | | |
| Total CAN system | | 1.5 | 1.14 | 1.5 |
| silicone DC-200 | | 15 | 15 | 15 |
| Ultrez-10 | | 0.3 | 0.3 | 0.3 |
| TEA to pH | | 8 | 7.8 | 7.8 |
| water | | qs100 | qs100 | qs100 |
| stability at 25° C., 43° C. and 50° C. at 30 days | | stable | unstable | unstable |

*CAN system = cationic, anionic, nonionic or bridge surfactants

EXAMPLE 7

As shown in TABLE 7 o/w emulsions are formed using the following systems. The same procedure was used per Example 5 above, with the temperature being about 70° C. The ratio between the anionic:cationic:bridge was 1:1:1 mole ratio.

TABLE 7

| O/W Emulsions 37 | | #37 % active |
|---|---|---|
| Anionic surfactant | STCS370 | |
| Cationic surfactant | Amm-GA | |
| Bridge surfactant | AMPHCA | |
| Total CAN system | | 1.5 |
| IPP | | 15 |
| Ultrez-10 | | 0.3 |
| TEA to pH | | 6 |
| water | | qs100 |
| stability at 25° C., 43° C. and 50° C. at 30 days | | stable |

| O/W Emulsions 38 | | #38 % active |
|---|---|---|
| Anionic surfactant | RM-1 | |
| Cationic surfactant | Cetac | |
| Bridge surfactant | AMPHCA | |
| Total CAN system | | 6 |
| mineral oil | | 70 |
| water | | qs 100 |
| stability at 25° C., 43° C. and 50° C. at 30 days | | stable |

*CAN system = cationic, anionic, nonionic or bridge surfactants

EXAMPLE 8

As shown in TABLE 8 a stable o/w emulsion was obtained when the anionic, cationic, bridge system (1:1:1 mole ratio) was used as an emulsifier system for a sunscreen formulation. The result sindicate that the system can provide suspension capabilities for physical sunscreens.

TABLE 8

| O/W Emulsions 39 | | #37 % active |
|---|---|---|
| Anionic surfactant | STCS370 | |
| Cationic surfactant | BTC65NF | |
| Bridge surfactant | AMXLO | |
| Total CAN system | | 1.7 |
| Elefac I-205 | | 15 |
| Kessco octylisononanoate | | 15 |
| Micro LA-20 | | 10 |
| Carbopol Ultrez 10 | | 0.3 |
| water | | qs100 |
| stability at 25° C., 43° C. and 50° C. at 30 days | | stable |

*CAN system = cationic, anionic, nonionic or bridge surfactants

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What is claimed is:
1. An emulsion comprising:
 (a) from about 0.3% to about 15% by weight, based on the total weight of the emulsion, of an emulsification system comprising:
  i) from about 0.1% to about 8% by weight, based on the total weight of the emulsion, of a cationic surfactant;
  ii) a from about 0.1% to about 8% by weight, based a on the total weight of the emulsion, of an anionic surfactant;
  iii) from about 0.1% to about 8% by weight, based on the total weight of the emulsion, of a bridging surfactant;
 (b) from about 3% to about 70% by weight, based on the total weight of the emulsion, of an oil; and
 (c) from about 15% to about 97% by weight, based on the total weight of the emulsion, of water;
wherein the emulsion is stable for at least 30 days at 25° C. in the absence of auxiliary co-emulsifiers.

2. An emulsion according to claim 1, comprising from about 0.3% to about 10% by weight, based on the total weight of the emulsion, of the emulsification system; from about 3% to about 70% by weight, based on the total weight of the emulsion, of an oil; and from about 6% to about 95% by weight, based on the total weight of the emulsion, of water.

3. An emulsion according to claim 1, wherein the cationic surfactant is a quaternary ammonium compound of the formula:

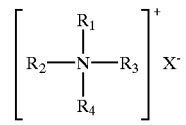

where
 $R_1$, $R_2$, and $R_3$ are independently ethyl, methyl or benzyl;
 $R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; or is a compound of the general formula (I)

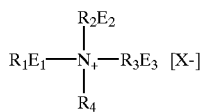

wherein X⁻ is an anion, $R_1$, $R_2$, $R_3$ can be the same or different and are independently straight or branched chain alkyl groups of from 2 to about 6 carbon atoms; R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

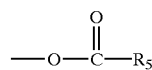

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II);

or a mixture thereof.

4. An emulsion according to claim 1, wherein the anionic surfactant is (a) an alkyl sulfate having an average of from about 8 to about 16 carbon atoms;

(b) an alkyl sulfonate having an average of from about 8 to about 18 carbon atoms;

(c) an alkyl ether sulfate having an average of from about 8 to about 16 carbon atoms in the alkyl portion and from about 1 to about 30 moles of ethylene oxide;

(d) an α-olefin sulfonate having an average of from about 12 to about 18 carbon atoms;

(e) an α-sulfonated $C_1$–$C_6$ alkyl ester of a fatty acid having an average of from about 11 to about 16 carbon atoms;

(f) a sulfosuccinate having an average of from about 10 to about 16 carbon atoms;

(g) a sarcosinate having an average of from about 10 to about 16 carbon atoms; or (h) a sulfoacetate having an average of from about 12 to about 20 carbon atoms;

(i) a phthalamate; or mixtures thereof.

5. An emulsion according to claim 1, wherein the bridging surfactant selected from the group consisting of amine oxides, ethoxamides, and betaines, or a mixture thereof.

6. An emulsion according to claim 1, wherein the oil is a silicon oil, mineral oil, a cosmetic ester or petrolatum, or a mixture thereof.

7. An emulsion according to claim 1, wherein the molar ratio of cationic surfactant to anionic surfactant to bridging surfactant is about 1:1:1.

8. An emulsion according to claim 1, wherein the emulsion is stable at 43° C. for 30 days in the absence of auxiliary co-emulsifiers.

9. An emulsion according to claim 1, wherein the emulsion is stable at 50° C. for 30 days in the absence of auxiliary co-emulsifiers.

10. A diluted emulsion comprising the emulsion of claim 1, wherein the emulsion of claim 1 has been diluted with water, whereby the total concentration of oil is from about 5% to about 15% by weight, based on the total weight of the diluted emulsion and the diluted emulsion is stable and comprises a stable phase at 50° C. for 30 days.

11. An emulsion according to claim 4, wherein the anionic surfactant is an alkyl sulfate having an average of from about 10 to about 12 carbon atoms.

12. An emulsion according to claim 4, wherein the anionic surfactant is an α-sulfonated $C_1$–$C_6$ alkyl ester of a fatty acid having an average of from about 11 to about 16 carbon atoms.

13. An emulsion according to claim 4, wherein the anionic surfactant is an alkyl sulfonate having an average of about 8 carbon atoms.

14. An emulsion according to claim 4, wherein the anionic surfactant is a stearyl phthalamate.

15. An emulsion according to claim 4, wherein the anionic surfactant is an alkyl ether sulfate having an average of from about 8 to about 16 carbon atoms in the alkyl portion and from about 1 to about 30 moles of ethylene oxide.

16. An emulsion according to claim 1, wherein the emulsion is an oil-in-water emulsion.

17. An emulsion according to claim 4, wherein the emulsion is a water-in-oil emulsion.

18. An emulsion comprising:

(a) from about 0.3% to about 15% by weight, based on the total weight of the emulsion, of an emulsification system comprising:

i) from about 0.1% to about 8% by weight, based on the total weight of the emulsion, of a cationic surfactant of the formula:

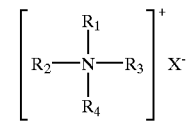

where $R_1$, $R_2$, and $R_3$ are independently ethyl, methyl or benzyl;

$R_4$ is an alkyl group having an average of from about 8 to about 18 carbon atoms; and X is halogen, sulfate, methosulfate, ethosulfate, tosylate, acetate, phosphate, nitrate, sulfonate, or carboxylate; or a cationic surfactant of the formula:

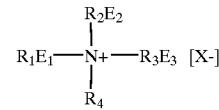

wherein X⁻ is an anion, $R_1$, $R_2$, $R_3$ can be the same or different and are independently straight or branched chain alkyl groups of from 2 to about 6 carbon atoms;

R4 is a saturated or unsaturated, straight or branched chain aliphatic group having from about 1 to about 6 carbon atoms optionally substituted with hydroxy, epoxy or halogen and $E_1$, $E_2$ and $E_3$ can be the same or different at each occurrence and are selected from the group consisting of —H, —OH and aliphatic ester groups of the following formula (II):

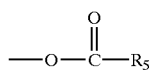

(II)

wherein $R_5$ is a saturated or unsaturated, straight or branched chain aliphatic group of from about 11 to about 24 carbon atoms, optionally substituted with hydroxy, epoxy or halogen, provided that at least one of $E_1$, $E_2$ or $E_3$ is a group of formula (II); or a mixture thereof;

ii) a from about 0.1% to about 8% by weight, based on the total weight of the emulsion, of an anionic surfactant which is
  a) an alkyl sulfate having an average of from about 8 to about 16 carbon atoms;
  b) an alkyl sulfonate having an average of from about 8 to about 18 carbon atoms;
  c) an alkyl ether sulfate having an average of from about 8 to about 16 carbon atoms in the alkyl portion and from about 1 to about 30 moles of ethylene oxide;
  d) an α-olefin sulfonate having an average of from about 12 to about 18 carbon atoms;
  e) an α-sulfonated $C_1$–$C_6$ alkyl ester of a fatty acid having an average of from about 11 to about 16 carbon atoms;
  f) a sulfosuccinate having an average of from about 10 to about 16 carbon atoms;
  g) a sarcosinate having an average of from about 10 to about 16 carbon atoms;
  h) a sulfoacetate having an average of from about 12 to about 20 carbon atoms;
  i) a phthalamate; or mixtures thereof; and iii) from about 0.1% to about 8% by weight, based on the total weight of the emulsion, of a bridging surfactant selected from the group consisting of amine oxides, ethoxamides, betaines, and mixtures thereof; and (b) from about 3% to about 70% by weight, based on the total weight of the emulsion, of an oil which is a silicon oil, mineral oil, a cosmetic ester or petrolatum, or a mixture thereof; and (c) from about 15% to about 97% by weight, based on the total weight of the emulsion, of water; wherein the emulsion is stable for at least 30 days at 25° C. in the absence of auxiliary co-emulsifiers.

19. An emulsion according to claim 18, comprising from about 0.3% to about 10% by weight, based on the total weight of the emulsion, of the emulsification system; from about 3% to about 70% by weight, based on the total weight of the emulsion, of an oil; and from about 6% to about 95% by weight, based on the total weight of the emulsion, of water.

20. An emulsion according to claim 19, wherein the molar ratio of cationic surfactant to anionic surfactant to bridging surfactant is about 1:1:1.

21. An emulsion according to claim 18, wherein the emulsion is stable at 43° C. for 30 days in the absence of auxiliary co-emulsifiers.

22. An emulsion according to claim 18, wherein the emulsion is stable at 50° C. for 30 days in the absence of auxiliary co-emulsifiers.

23. A diluted emulsion comprising the emulsion of claim 18, wherein the emulsion of claim 1 has been diluted with water, whereby the total concentration of oil is from about 5% to about 15% by weight, based on the total weight of the diluted emulsion and the diluted emulsion is stable and comprises a stable phase at 50° C. for 30 days.

24. An emulsion according to claim 18, wherein the emulsion is an oil-in-water emulsion.

25. An emulsion according to claim 18, wherein the emulsion is a water-in-oil emulsion.

26. An emulsion comprising:
  (a) from about 0.3% to about 15% by weight, based on the total weight of the emulsion, of an emulsification system comprising:
    i) from about 0.1% to about 8% by weight, based on the total weight of the emulsion, of a cationic surfactant;
    ii) a from about 0.1% to about 8% by weight, based on the total weight of the emulsion, of an anionic surfactant;
    iii) from about 0.1% to about 8% by weight, based on the total weight of the emulsion, of a bridging surfactant;
  (b) from about 50% to about 70% by weight, based on the total weight of the emulsion, of an oil; and
  (c) from about 15% to about 49% by weight, based on the total weight of the emulsion, of water;
wherein the emulsion is stable for at least 30 days at 25° C. in the absence of auxiliary co-emulsifiers.

27. A diluted emulsion comprising the emulsion of claim 26, wherein the emulsion of claim 1 has been diluted with water, whereby the total concentration of oil is from about 5% to about 15% by weight, based on the total weight of the diluted emulsion and the diluted emulsion is stable and comprises a stable phase at 50° C. for 30 days.

28. A method for preparing an emulsion comprising combining in any order:
  (a) from about 0.3% to about 15% by weight, based on the total weight of the emulsion, of an emulsification system comprising:
    i) from about 0.1% to about 8% by weight, based on the total weight of the emulsion, of a cationic surfactant;
    ii) a from about 0.1% to about 8% by weight, based on the total weight of the emulsion, of an anionic surfactant;
    iii) from about 0.1% to about 8% by weight, based on the total weight of the emulsion, of a bridging surfactant;
  (b) from about 3% to about 70% by weight, based on the total weight of the emulsion, of an oil; and
  (c) from about 15% to about 97% by weight, based on the total weight of the emulsion, of water;
wherein the emulsion is stable for at least 30 days at 25° C. in the absence of auxiliary co-emulsifiers.

29. A method for preparing an emulsion according to claim 28, further comprising diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 50° C. for 30 days.

30. A method for preparing an emulsion comprising combining in any order:
  (a) from about 0.3% to about 15% by weight, based on the total weight of the emulsion, of an emulsification system comprising:
    i) from about 0.1% to about 8% by weight, based on the total weight of the emulsion, of a cationic surfactant;

ii) a from about 0.1% to about 8% by weight, based on the total weight of the emulsion, of an anionic surfactant;

iii) from about 0.1% to about 8% by weight, based on the total weight of the emulsion, of a bridging surfactant;

(b) from about 50% to about 70% by weight, based on the total weight of the emulsion, of an oil; and (c) from about 15% to about 49% by weight, based on the total weight of the emulsion, of water;

wherein the emulsion is stable for at least 30 days at 25° C. in the absence of auxiliary co-emulsifiers.

31. A method for preparing an emulsion according to claim 30, further comprising diluting the emulsion with water to form a diluted emulsion, whereby the total concentration of oil in the diluted emulsion is from about 5% to about 15% by weight, based on the total weight of the diluted emulsion and the diluted emulsion is stable and comprises a stable phase at 50° C. for 30 days.

32. A stable particulate matter suspension comprising:

(a) from about 0.3% to about 15% by weight, based on the total weight of the particulate matter suspension, of a suspension system comprising:

i) from about 0.1% to about 8% by weight, based on the total weight of the particulate matter suspension, of a cationic surfactant;

ii) from about 0.1% to about 8% by weight, based on the total weight of the particulate matter suspension, of an anionic surfactant;

iii) from about 0.1% to about 8% by weight, based on the total weight of the particulate matter suspension, of a bridging surfactant;

(b) from about 3% to about 70% by weight, based on the total weight of the particulate matter suspension, of solid particulate matter; and (c) from about 15% to about 97% by weight, based on the total weight of the particulate matter suspension, of water;

wherein the emulsion is stable for at least 30 days at 25° C. in the absence of auxiliary co-emulsifiers.

33. A stable particulate matter suspension according to claim 32, wherein the solid particulate matter is an inorganic sunscreen, a powder, a pigment, an abrasive, a coal tar, an antidandruff agent or a mixture thereof.

34. A stable sunscreen emulsion comprising:

(a) from about 0.3% to about 15% by weight, based on the total weight of the sunscreen emulsion, of an emulsification system comprising:

i) from about 0.1% to about 8% by weight, based on the total weight of the sunscreen emulsion, of a cationic surfactant;

ii) a from about 0.1% to about 8% by weight, based on the total weight of the sunscreen emulsion, of an anionic surfactant;

iii) from about 0.1% to about 8% by weight, based on the total weight of the sunscreen emulsion, of a bridging surfactant;

(b) from about 3% to about 70% by weight, based on the total weight of the sunscreen emulsion, of an oil;

(c) from about 15% to about 97% by weight, based on the total weight of the sunscreen emulsion, of water; and (d) from about 0.1% to about 10% by weight, based on the weight of the sunscreen emulsion, of a sunscreen;

wherein the emulsion is stable for at least 30 days at 25° C. in the absence of auxiliary co-emulsifiers.

35. A sunscreen emulsion according to claim 34, wherein the sunscreen absorbs UVA and UVB radiation or UVA or UVB radiation.

36. A sunscreen emulsion according to claim 35, wherein the sunscreen is selected from the group consisting of hexyl-p-methoxy-cinnamate, benzophenone-3, 2-phenylbenzimidazole-5-sulfonic acid, octyldimethyl p-amino benzoic acid, micronized titanium dioxide, or zinc oxide, or a mixture thereof.

37. A sunscreen emulsion according to claim 36, wherein the sunscreen is an inorganic sunscreen capable of scattering, reflecting and absorbing UV radiation.

* * * * *